(12) United States Patent
Liu et al.

(10) Patent No.: US 8,729,241 B2
(45) Date of Patent: May 20, 2014

(54) CHARACTERIZATION OF O-LINKED GLYCANS

(75) Inventors: Cuihua Liu, Belmont, MA (US); Xiao-Jin Xu, Jamaica Plain, MA (US); Shiming Dong, North Reading, MA (US); Guy Dellorusso, Milford, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 173 days.

(21) Appl. No.: 13/140,550

(22) PCT Filed: Dec. 18, 2009

(86) PCT No.: PCT/US2009/068769
§ 371 (c)(1), (2), (4) Date: Aug. 2, 2011

(87) PCT Pub. No.: WO2010/071817
PCT Pub. Date: Jun. 24, 2010

(65) Prior Publication Data
US 2011/0287465 A1    Nov. 24, 2011

Related U.S. Application Data

(60) Provisional application No. 61/139,048, filed on Dec. 19, 2008.

(51) Int. Cl.
*C08B 37/00* (2006.01)
*G01N 30/72* (2006.01)

(52) U.S. Cl.
CPC .............. *C08B 37/00* (2013.01); *G01N 30/72* (2013.01)
USPC ........................................ 530/395; 514/20.9

(58) Field of Classification Search
None
See application file for complete search history.

(56) References Cited

U.S. PATENT DOCUMENTS

| | | |
|---|---|---|
| 2006/0057638 A1 | 3/2006 | Bosques et al. |
| 2007/0105179 A1 | 5/2007 | Madson |

FOREIGN PATENT DOCUMENTS

| | | | | |
|---|---|---|---|---|
| WO | WO02/06295 | * | 1/2002 | ............... C07H 1/08 |

OTHER PUBLICATIONS

Schapira et al., "Serum Erythropoietin Levels in Patients Receiving Intensive Chemotherapy and Radiotherapy" Blood (1990) vol. 76 No. 11 pp. 2354-2359.*
Gonzalez-Quintela et al., "Serum levels of immunoglobulins (IgG, IgA, IgM) in a general adult population and their relationship with alcohol consumption, smoking and common metabolic abnormalities" Clinical and Experimental Immunology (2007) vol. 151 pp. 42-50.*
Ytterberg et al., "Serum Interferon Levels in Patients With Systemic Lupus Erythematosus" Arthritis and Rheumatism (1982) vol. 25 No. 4 pp. 401-406.*
Sudlow et al., "Further Characterization of Specific Drug Binding Sites on Human Serum Albumin" Molecular Pharmacology (1976) vol. 12 pp. 1052-1061.*
Anumula, KR, "Advances in fluorescence derivatization methods for high-performance liquid chromatographic analysis of glycoprotein carbohydrates," *Anal. Biochem.* 350(1): 1-23, 2006.
Carlson, Don M., "Structures and Immunochemical Properties of Oligosaccharides Isolated from Pig Submaxillary Mucins," *The Journal of Biological Chemistry*, 242(3): 616-626, 1968.
Dalpathado, Dilusha S., et al., "Glycopeptide analysis by mass spectrometry," *Analyst*, 133: 731-738, 2008.
Deguchi, Kisaburo, et al., "Structural analysis of O-glycopeptides employing negative- and positive-ion multi-stage mass spectra obtained by collision-induced and electron-capture dissociations in linear ion trap time-of-flight mass spectrometry," *Rapid Commun. Mass Spectrom.* 21: 691-698, 2007.
Greis, Kenneth D., et al., "Selective Detection and Site-Analysis of O-GlcNAc-Modified Glycopeptides by β-Elimination and Tandem Electrospray Mass Spectromety," *Anal. Biochem.* 234: 38-49, 1996.
Hanisch, Franz-Georg, et al., "Glycoprotein Identification and Localization of O-Glycosylation Sites by Mass Spectrometric Analysis of Deglycosylated/Alkylaminylated Peptide Fragments," *Anal. Biochem.* 290: 47-59, 2001.
Huang, Yunping, et al., "Matrix-assisted laster desorption/ionization mass spectrometry compatible β-elimination of O-linked oligosaccharides," *Rapid Commun. Mass Spectrom.* 16: 1199-1204, 2002.
Huang, Yunping, et al., "Microscale Nonreductive Release of 0-Linked Glycans for Subsequent Analysis through Maldi Mass Spectrometry and Capillary Electroporesis," Anal. Chem., 73(24): 6063-6069, 2001.
Lis, Halina, et al., "Protein glycoslyation," *Eur J. Biochem.* 218: 1-27, 1993.
Morelle, Willy, et al, "Analysis of protein glycosylation by mass spectrometry," *Nature Protocols*, 2(7): 1585-1602, 2007.
Patel, Thakor et al., "Use of Hydrazine to Release in Intact and Unreduced Form both N-and O-Linked Oligosaccharides from Glycoproteins," *Biochemistry* 32(2): 679-393, 1993.
Rademaker, Geert Jan, et al., "Mass Spectrometric Determination of the Sites of O-Glycan Attachment with Low Picomolar Sensitivity," *Anal. Biochem.* 257: 149-160, 1998.

(Continued)

*Primary Examiner* — Eric S Olson
(74) *Attorney, Agent, or Firm* — Choate, Hall & Stewart LLP; Brenda H. Jarrell; Rolando Medina

(57) ABSTRACT

The present disclosure provides methods for analyzing structure and/or composition of glycoproteins and glycans of glycoproteins. Such methods can include subjecting a glycoprotein preparation to a condition that removes at least one O-linked glycan from the glycoprotein. Such methods can include subjecting a glycoprotein preparation to a condition that releases an N-glycan from the glycoprotein, e.g., prior to subjecting the glycoprotein to a condition that releases an O-glycan from the glycoprotein.

14 Claims, 7 Drawing Sheets

(56) References Cited

OTHER PUBLICATIONS

Wopereis et al., "Mechanisms in protein O-glycan biosynthesis and clinical and molecular aspects of protein O-glycan biosynthesis defects: a review," *Clin. Chem.* 52(4): 574-600, 2006.

Written Opinion for PCT/US09/068769 mailed on Sep. 15, 2010.

Xie, Yongming, et al., "Method for the Comparative Glycomic Analyses of O-Linked, Mucin-Type Oligosaccharides," *Anal. Chem.*, 76(17): 5186-5197, 2004.

Zhang, Jinhua, et al., "Profiling the morphological distribution of O-linked oligosaccharides," *Anal. Biochem.* 334: 20-35, 2004.

Faid et al., "A rapid mass spectrometric strategy for the characterization of N- and O-glycan chains in the diagnosis of defects in glycan biosynthesis" *Proteomics* 7(11):1800-1813 (2007).

Sakaguchi et al., "Isolation of the reducing oligosaccharide chains from the chondroitin/dermatan sulfate-protein linkage region and preparation of analytical probes by fluorescent labeling with 2-aminobenzamide" *J. Biochem.* 129(1):107-118 (2001).

Supplementary European Search Report, EP 09 83 3841, mailed on May 10, 2012.

Wilson et al., "Sequential Analysis of N- and O-Linked Glycosylation of 2D-PAGE Separated Glycoproteins" *J. Proteome Res.* 1(6):521-529 (2002).

\* cited by examiner

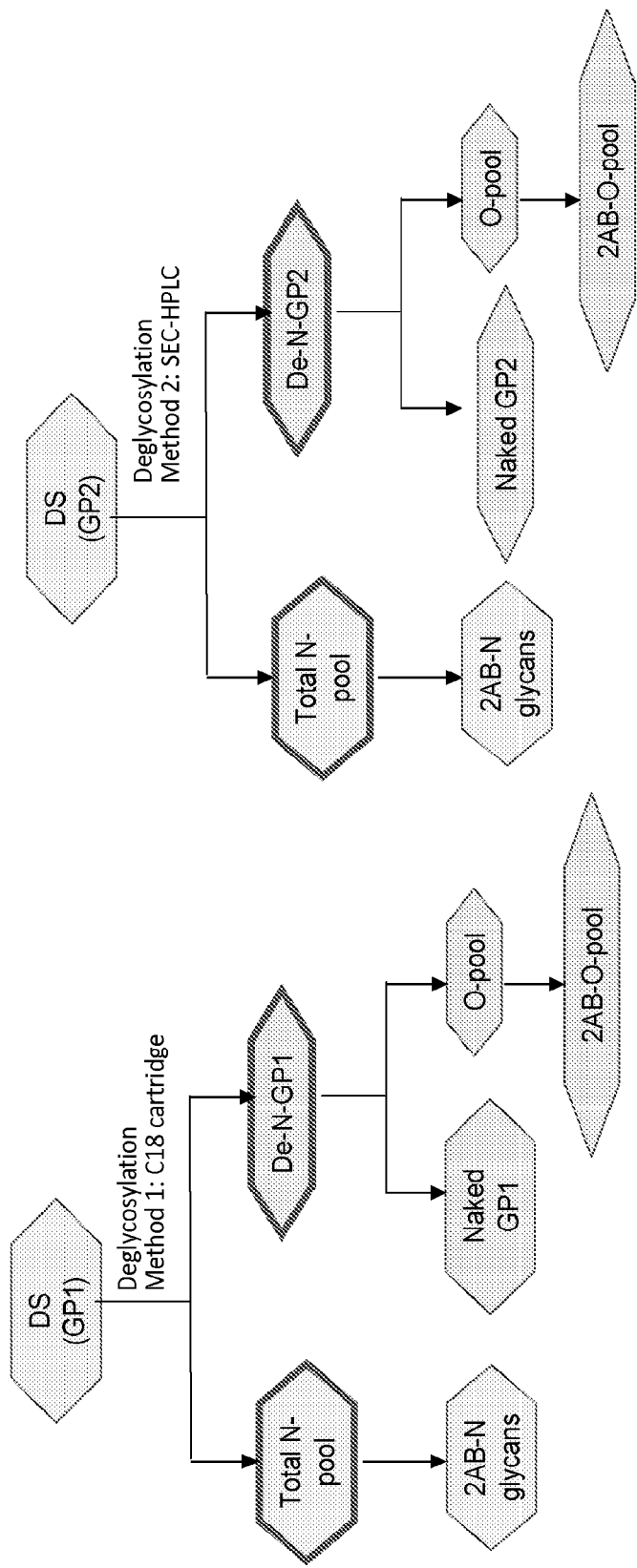
Fig 1. Schematic diagram of an exemplary workflow applied to a smaller glycoprotein (GP1), e.g., less than 30 kDa and a larger glycoprotein, e.g., greater than or equal to 30 kDa.

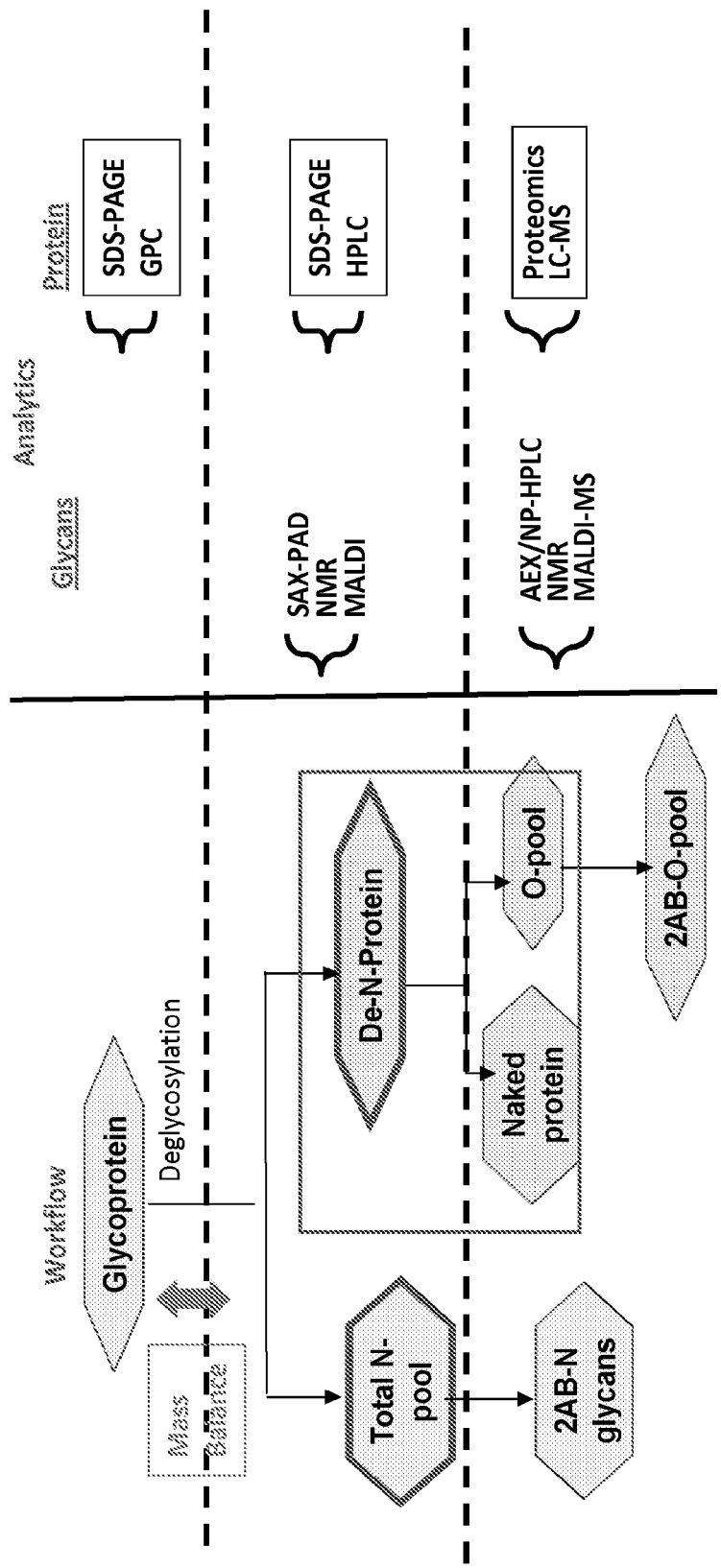
Fig 2. Schematic diagram of an exemplary analytics for analysis of sample derived from each step of the workflow shown in Fig 1.

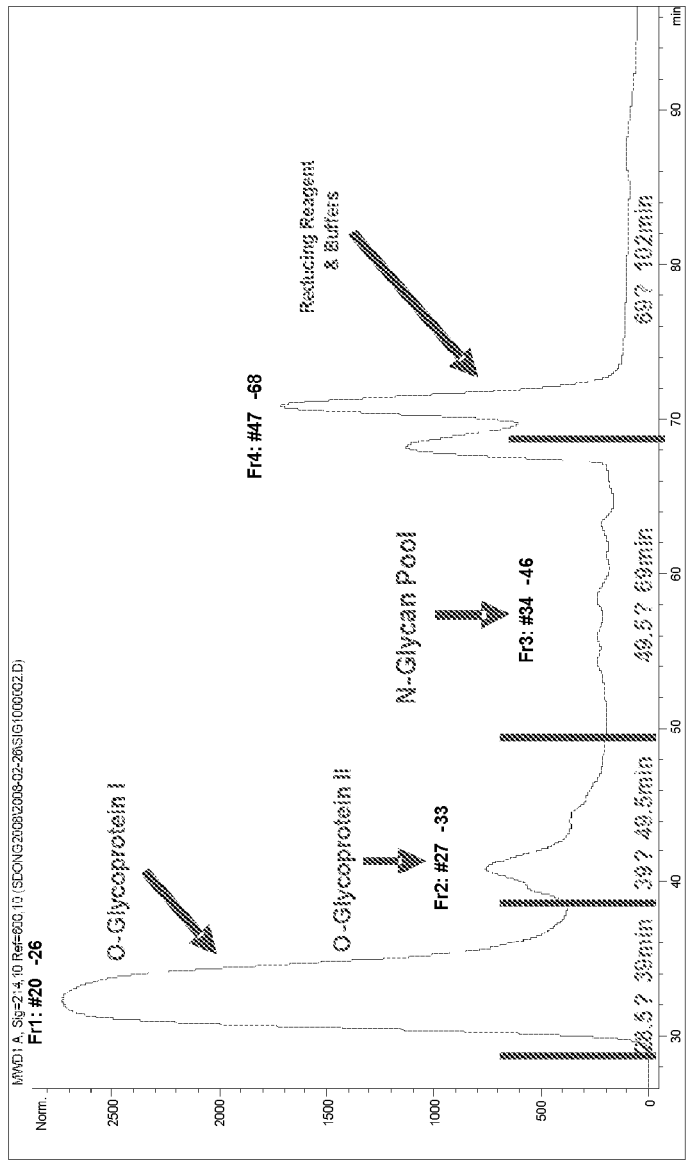
Fig 3. Chromatogram of SEC-HPLC analysis of larger glycoproteins treated in described in Example 1.

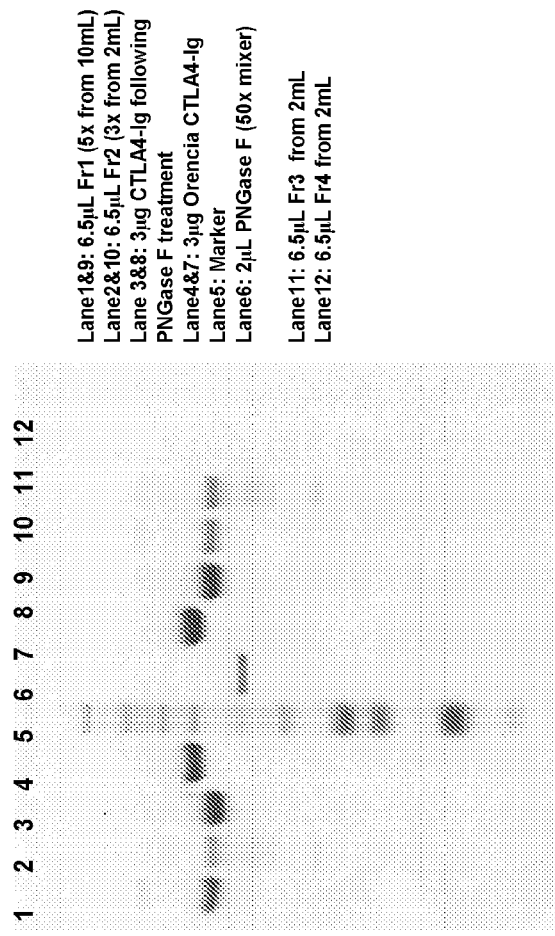
Fig 4. Photograph of an electrophoretic analysis of larger glycoproteins CTLA4Ig and Orencia® glycoprotein, treated as described in Example 1.

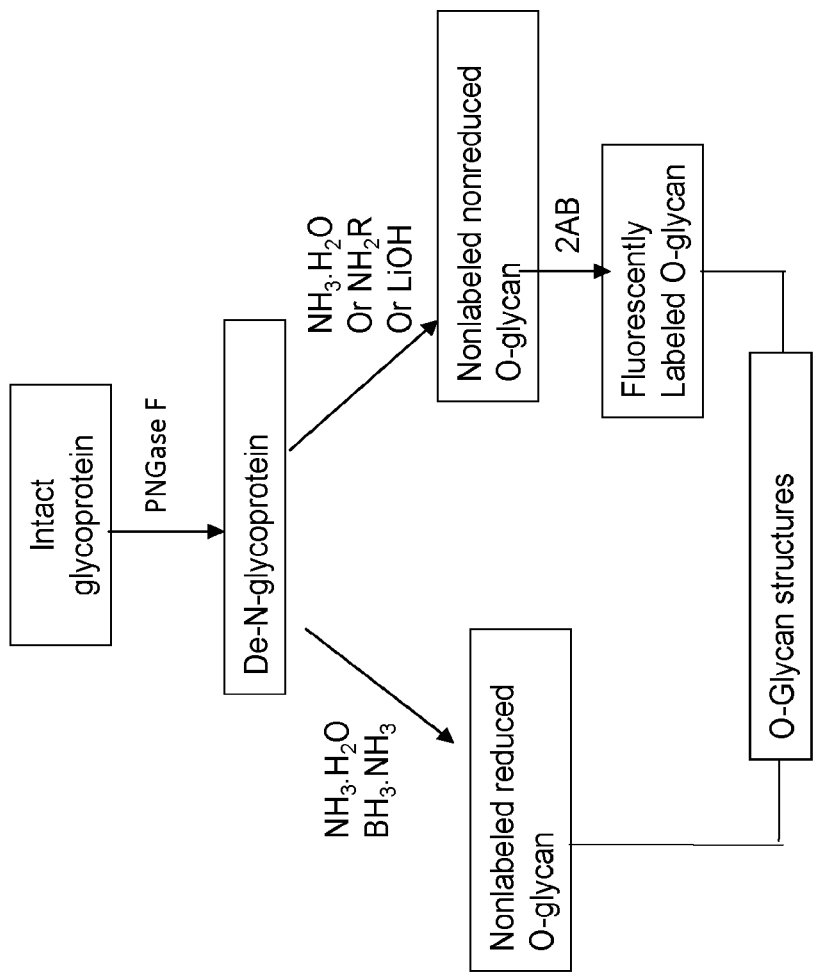
Fig 5. Schematic diagram of an exemplary workflow applied to analysis of O-glycans of any glycoprotein

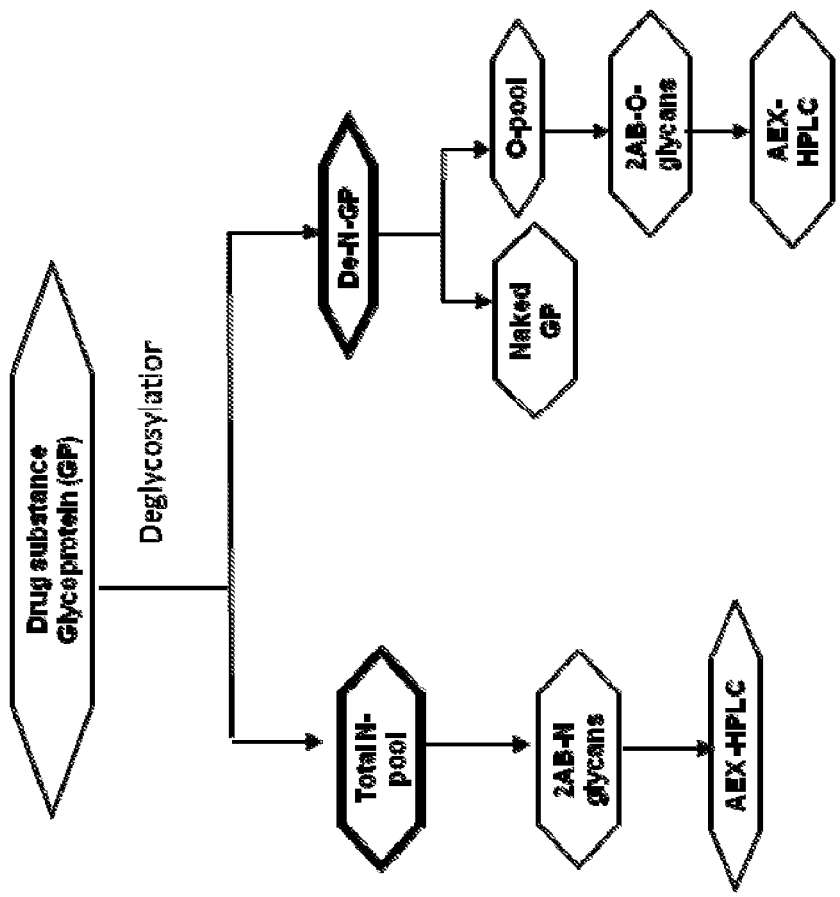
Fig 6. Schematic diagram of an exemplary workflow applied to a drug substance glycoprotein.

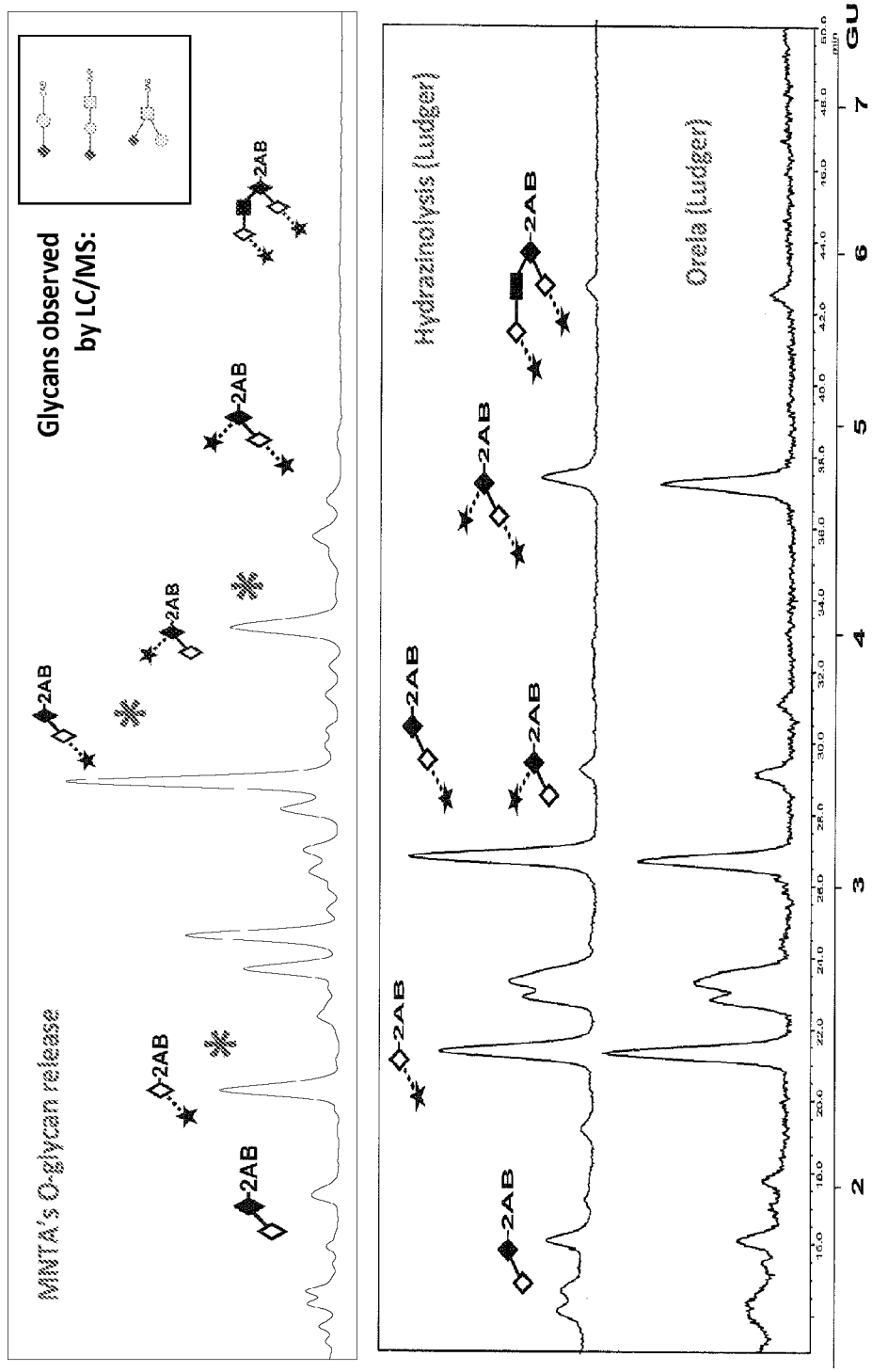
Fig 7. Comparison of graphs of NP-HPLC profiles of glycans released by the described O-glycan release method of LiOH (top panel). The middle and bottom panels were obtained from Ludger's commercial catalogs. hydranzinolysis from Ludger (middle panel) or Ludger's Orela method (bottom panel), from a Fetuin glycoprotein.

CHARACTERIZATION OF O-LINKED GLYCANS

The present application claims the benefit under 35 U.S.C. §371 of International Application No. PCT/US09/68796, filed Dec. 18, 2009, which claims priority to U.S. Provisional patent application Ser. No. 61/139,048, filed on Dec. 19, 2008, the entire disclosure of which is incorporated herein by reference.

BACKGROUND

Glycosylation often plays a significant role in the biological function(s) of glycoconjugates (e.g., glycoproteins). For example, a glycoprotein's glycosylation pattern may affect its ability to fold correctly, its stability (e.g., resistance to proteolytic and/or other degradation), catalytic activity, pharmacodynamic and/or pharmacokinetic properties, and/or the ability of that glycoprotein to properly interact with other molecules. Alternatively or additionally, a glycoprotein's glycosylation pattern can affect transport and targeting of the glycoprotein, e.g., determining whether the glycoprotein remains intracellular (including, e.g., the correct targeting of the glycoprotein to the proper subcellular compartment or compartments), whether the glycoprotein will be membrane-bound and/or whether the glycoprotein will be secreted from the cell.

Individual glycoproteins often have more than one site for attachment of glycans by either N-linkages, O-linkages, or both. O-glycosylation processes produce a huge diversity of glycan structures. Given the importance of glycosylation in glycoprotein or glycoconjugate function, methods to characterize and quantify O-glycan species on glycoconjugates are needed.

SUMMARY

The present disclosure provides methods of analyzing glycans, and particularly of analyzing O-linked glycans. According to the present disclosure, methods described herein can be used to analyze and/or quantitate O-linked glycans. In some embodiments, methods described herein are used to analyze and/or quantitate O-linked glycans and N-linked glycans of a glycoconjugate preparation.

A method for analyzing glycans can include providing a glycoconjugate (e.g., a glycoprotein) preparation comprising at least one O-linked glycan; releasing at least one O-linked glycan from the glycoconjugate preparation by β-elimination; and analyzing the at least one released O-linked glycan. In some embodiments, the β-elimination is reductive β-elimination. In some embodiments, the β-elimination is non-reductive β-elimination.

In some embodiments, a glycoconjugate preparation includes a glycoprotein suspected of including O-linked glycans. In some embodiments, a glycoconjugate preparation includes a glycoprotein suspected of including O-linked glycans and lacking N-linked glycans. In some embodiments, a glycoconjugate preparation includes a glycoprotein suspected of including O-linked glycans and N-linked glycans.

In some embodiments, releasing at least one O-linked glycan from a glycoprotein preparation includes administering NaOH and NaBH$_4$ to the glycoprotein preparation. In some embodiments, releasing at least one O-linked glycan from a glycoprotein preparation comprises administering NH$_3$H$_2$O to the glycoprotein preparation. In some embodiments, releasing at least one O-linked glycan from a glycoprotein preparation comprises administering NH$_3$H$_2$O and BH$_3$NH$_3$ to the glycoprotein preparation. In some embodiments, releasing at least one O-linked glycan from a glycoprotein preparation comprises administering LiOH to the glycoprotein preparation.

Provided methods can include labeling at least one O-linked glycan. For example, in some embodiments, at least one released O-linked glycan is labeled with 2-aminobenzamide.

Provided methods can include isolating at least one released O-linked glycan from a glycoconjugate preparation.

In some embodiments, analyzing includes subjecting at least one released O-linked glycan to mass spectrometry. In some embodiments, analyzing includes subjecting at least one released O-linked glycan to liquid chromatography and mass spectrometry (LC-MS).

In some embodiments, provided methods include quantifying at least one released O-linked glycan. Methods can further include analyzing a glycoprotein preparation, after release of O-linked glycans.

The present disclosure also features a method that includes providing a glycoprotein preparation comprising at least one O-linked glycan; subjecting the glycoprotein preparation to a de-N-glycosylation treatment that removes N-glycans from the glycoprotein preparation; releasing at least one O-linked glycan from the treated glycoprotein preparation by β-elimination; and analyzing the at least one released O-linked glycan.

In some embodiments, removing N-glycans from a glycoprotein preparation includes administering PGNase F to the glycoprotein preparation. In some embodiments, removing N-glycans from a glycoprotein preparation includes administering hydrazine to the glycoprotein preparation. In some embodiments, at least about 80%, 85%, 90%, 95%, 97%, 99%, 99.5%, 99.9%, or 100% of N-glycans are removed from the glycoprotein preparation. Provided methods can further include isolating de-N-glycosylated glycoproteins from released N-glycans.

In some embodiments of provided methods, β-elimination is reductive β-elimination.

In some embodiments of provided methods, β-elimination is non-reductive β-elimination.

In some embodiments, release of at least one O-linked glycan from a glycoprotein preparation includes administering NaOH and NaBH$_4$ to the glycoprotein preparation. In some embodiments, release of at least one O-linked glycan from a glycoprotein preparation includes administering NH$_3$H$_2$O to the glycoprotein preparation.

Releasing at least one O-linked glycan from a glycoprotein preparation can include administering NH$_3$H$_2$O and BH$_3$NH$_3$ to the glycoprotein preparation.

Releasing at least one O-linked glycan from a glycoprotein preparation can include administering LiOH to the glycoprotein preparation.

Provided methods can further include labeling at least one released O-linked glycan, e.g., by administering 2-aminobenzamide, 2-aminopurine, or 2-aminobenzoic acid, prior to or after release of the O-linked glycan.

Provided methods can further include isolating at least one released O-linked glycan (e.g., with a C18 cartridge, or a porous graphitized carbon cartridge).

Such analyzing can include subjecting at least one released O-glycan to mass spectrometry (e.g., MALDI-MS), NMR, or to liquid chromatography and mass spectrometry. In some embodiments, provided methods include quantifying at least one released O-linked glycan. In some embodiments, provided methods include analyzing N-glycans, and/or the glycoprotein preparation, after one or both of the treatments to release N- and O-linked glycans.

The present disclosure further provides methods including: providing a glycoprotein preparation comprising at least one O-linked glycan; subjecting the glycoprotein preparation to a de-N-glycosylation treatment that removes N-glycans from the glycoprotein preparation; digesting the treated glycoprotein preparation; releasing at least one O-linked glycan from the de-N-glycosylated and digested glycoprotein preparation by β-elimination; and analyzing the at least one released O-linked glycan.

In some embodiments, digesting the de-N-glycosylated glycoprotein preparation includes administering an enzyme to the de-N-glycosylated glycoprotein preparation. In some embodiments, digesting the de-N-glycosylated glycoprotein includes administering a chemical cleavage agent to the de-N-glycosylated glycoprotein preparation.

The present disclosure further provides methods including: providing a first and second glycoprotein preparation comprising at least one O-linked glycan; releasing at least one O-linked glycan from the first and second glycoprotein preparations by β-elimination; analyzing the at least one released O-linked glycan obtained from the first and second glycoprotein preparations.

In some embodiments, provided methods comprise a step of subjecting the first and second glycoprotein preparations to a de-N-glycosylation treatment that removes N-glycans from the glycoprotein preparations.

In some embodiments, the β-elimination of the first glycoprotein preparation is reductive β-elimination and the β-elimination of the second glycoprotein preparation is non-reductive β-elimination.

In some embodiments, provided methods comprise a step of comparing a result of the analysis of the at least one released O-linked glycan obtained from the first glycoprotein preparation with a result of the analysis of the at least one released O-linked glycan obtained from the second glycoprotein preparation.

In some embodiments, the second glycoprotein preparation comprises a glycoprotein having an amino acid sequence at least 85% identical to an amino acid sequence of the glycoprotein in the first glycoprotein preparation.

In some embodiments, the released O-linked glycan of one or both of the preparations comprises a label.

The present disclosure further provides methods including: providing a glycoprotein preparation comprising at least one O-linked glycan; subjecting the glycoprotein preparation to a de-N-glycosylation treatment that removes N-glycans from the glycoprotein preparation; releasing at least one O-linked glycan from a first portion of the treated glycoprotein sample by reductive β-elimination, releasing at least one O-linked glycan from a second portion of the treated glycoprotein sample by non-reductive β-elimination; and analyzing the released O-linked glycans from the first and second portions of the treated glycoprotein sample.

In some embodiments, released O-glycans from the first and/or second portions of the treated glycoprotein samples are labeled.

In some embodiments, provided methods further comprise repeating the method with a second glycoprotein preparation. In some embodiments, a result of analysis of released O-linked glycans obtained from the first glycoprotein preparation is compared with a result of the analysis of released O-linked glycans obtained from the second glycoprotein preparation.

In some embodiments, the second glycoprotein preparation comprises a glycoprotein having an amino acid sequence at least 85% identical to an amino acid sequence of the glycoprotein in the first glycoprotein preparation.

BRIEF DESCRIPTION OF THE DRAWING

FIG. 1 is a schematic diagram of an exemplary workflow applied to a smaller glycoprotein, e.g., less than 30 kDa (GP1) and a larger glycoprotein, e.g., greater or equal to 30 kDa (GP2).

FIG. 2 is a schematic diagram of an exemplary analytics matrix for analysis of samples derived from each step of the workflow shown in FIG. 1.

FIG. 3 is a graph showing peaks from SEC-HPLC analysis of larger glycoproteins treated as described in Example 1.

FIG. 4 is a photograph of an electrophoretic analysis of larger glycoproteins CTLA4-Ig and Orencia® glycoproteins, treated as described in Example 1.

FIG. 5 is a schematic diagram of an exemplary workflow applied to analysis of O-glycans of any glycoprotein.

FIG. 6 is a schematic diagram of an exemplary workflow applied to a drug substance glycoprotein.

FIG. 7 is a set of graphs showing NP-HPLC profiles of glycans released by a described O-glycan release method (top panel), hydrazinolysis (middle panel) or Ludger's method (bottom panel), from a Fetuin glycoprotein.

DEFINITIONS

Approximately, About, Ca.: As used herein, the terms "approximately", "about" or "ca.," as applied to one or more values of interest, refer to a value that is similar to a stated reference value. In certain embodiments, the terms "approximately", "about" or "ca.," refer to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less of the stated reference value.

Biological sample: The term "biological sample," as used herein, refers to any solid or fluid sample obtained from, excreted by or secreted by any living cell or organism, including, but not limited to, tissue culture, bioreactor sample, human or animal tissue, plants, fruits, vegetables, single-celled microorganisms (such as bacteria and yeasts) and multicellular organisms. For example, a biological sample can be a biological fluid obtained from, e.g., blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, e.g., a sample obtained from any organ or tissue (including a biopsy or autopsy specimen), can comprise cells (whether primary cells or cultured cells), medium conditioned by any cell, tissue or organ, tissue culture.

Cell-surface glycoprotein: As used herein, the term "cell-surface glycoprotein" refers to a glycoprotein, at least a portion of which is present on the exterior surface of a cell. In some embodiments, a cell-surface glycoprotein is a protein that is positioned on the cell surface such that at least one of the glycan structures is present on the exterior surface of the cell.

Cell-surface glycan: A "cell-surface glycan" is a glycan that is present on the exterior surface of a cell. In many embodiments of the present disclosure, a cell-surface glycan is covalently linked to a polypeptide as part of a cell-surface glycoprotein. A cell-surface glycan can also be linked to a cell membrane lipid.

Glycan: As is known in the art and used herein "glycans" are sugars. Glycans can be monomers or polymers of sugar residues, but typically contain at least three sugars, and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'sulfo N-acetylglucosamine, etc.). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

Glycan preparation: The term "glycan preparation" as used herein refers to a set of glycans obtained according to a particular production method. In some embodiments, glycan preparation refers to a set of glycans obtained from a glycoprotein preparation (see definition of glycoprotein preparation below).

Glycoconjugate: The term "glycoconjugate," as used herein, encompasses all molecules in which at least one sugar moiety is covalently linked to at least one other moiety. The term specifically encompasses all biomolecules with covalently attached sugar moieties, including for example N-linked glycoproteins, O-linked glycoproteins, glycolipids, proteoglycans, etc.

Glycoform: The term "glycoform," is used herein to refer to a particular form of a glycoconjugate. That is, when the same backbone moiety (e.g., polypeptide, lipid, etc) that is part of a glycoconjugate has the potential to be linked to different glycans or sets of glycans, then each different version of the glycoconjugate (i.e., where the backbone is linked to a particular set of glycans) is referred to as a "glycoform."

Glycolipid: The term "glycolipid" as used herein refers to a lipid that contains one or more covalently linked sugar moieties (i.e., glycans). The sugar moiety(ies) may be in the form of monosaccharides, disaccharides, oligosaccharides, and/or polysaccharides. The sugar moiety(ies) may comprise a single unbranched chain of sugar residues or may be comprised of one or more branched chains. In certain embodiments, sugar moieties may include sulfate and/or phosphate groups. In certain embodiments, glycoproteins contain O-linked sugar moieties; in certain embodiments, glycoproteins contain N-linked sugar moieties.

Glycoprotein: As used herein, the term "glycoprotein" refers to a protein that contains a peptide backbone covalently linked to one or more sugar moieties (i.e., glycans). As is understood by those skilled in the art, the peptide backbone typically comprises a linear chain of amino acid residues. In certain embodiments, the peptide backbone spans the cell membrane, such that it comprises a transmembrane portion and an extracellular portion. In certain embodiments, a peptide backbone of a glycoprotein that spans the cell membrane comprises an intracellular portion, a transmembrane portion, and an extracellular portion. In certain embodiments, methods of the present disclosure comprise cleaving a cell surface glycoprotein with a protease to liberate the extracellular portion of the glycoprotein, or a portion thereof, wherein such exposure does not substantially rupture the cell membrane. The sugar moiety(ies) may be in the form of monosaccharides, disaccharides, oligosaccharides, and/or polysaccharides. The sugar moiety(ies) may comprise a single unbranched chain of sugar residues or may comprise one or more branched chains. In certain embodiments, sugar moieties may include sulfate and/or phosphate groups. Alternatively or additionally, sugar moieties may include acetyl, glycolyl, propyl or other alkyl modifications. In certain embodiments, glycoproteins contain O-linked sugar moieties; in certain embodiments, glycoproteins contain N-linked sugar moieties. In certain embodiments, methods disclosed herein comprise a step of analyzing any or all of cell surface glycoproteins, liberated fragments of cell surface glycoproteins, cell surface glycans attached to cell surface glycoproteins, peptide backbones of cell surface glycoproteins, fragments of such glycoproteins, glycans and/or peptide backbones, and combinations thereof. The terms "glycoprotein" and "glycopeptide" are used interchangeably herein.

Glycoprotein preparation: A "glycoprotein preparation," as that term is used herein, refers to a set of individual glycoprotein molecules, each of which comprises a polypeptide having a particular amino acid sequence (which amino acid sequence includes at least one glycosylation site) and at least one glycan covalently attached to the at least one glycosylation site. Individual molecules of a particular glycoprotein within a glycoprotein preparation typically have identical amino acid sequences but may differ in the occupancy of the at least one glycosylation sites and/or in the identity of the glycans linked to the at least one glycosylation sites. That is, a glycoprotein preparation may contain only a single glycoform of a particular glycoprotein, but more typically contains a plurality of glycoforms. Different preparations of the same glycoprotein may differ in the identity of glycoforms present (e.g., a glycoform that is present in one preparation may be absent from another) and/or in the relative amounts of different glycoforms. In some embodiments, the present invention provides methods and reagents for analyzing different preparations of the same glycoprotein (i.e., having identical amino acid sequence). In some embodiments, the present invention provides methods and reagents for analyzing preparations of two (or more) glycoproteins whose amino acid sequences show at least 85%, 90%, 91%, 92%, 93%, 94%, 95%, 96%, 97%, 98%, 99% identity, or greater.

Glycosidase: The term "glycosidase" as used herein refers to an agent that cleaves a covalent bond between sequential sugars in a glycan or between the sugar and the backbone moiety (e.g., between sugar and peptide backbone of glycoprotein). In some embodiments, a glycosidase is an enzyme. In certain embodiments, a glycosidase is a protein (e.g., a protein enzyme) comprising one or more polypeptide chains. In certain embodiments, a glycosidase is a chemical cleavage agent.

Glycosylation pattern: As used herein, the term "glycosylation pattern" refers to the set of glycan structures present on a particular sample. For example, a particular glycoconjugate (e.g., glycoprotein) or set of glycoconjugates (e.g., set of glycoproteins) will have a glycosylation pattern. In some embodiments, reference is made to the glycosylation pattern of cell surface glycans. A glycosylation pattern can be characterized by, for example, the identities of glycans, amounts (absolute or relative) of individual glycans or glycans of particular types, degree of occupancy of glycosylation sites, etc., or combinations of such parameters.

N-glycan: The term "N-glycan," as used herein, refers to a polymer of sugars that has been released from a glycoconjugate but was formerly linked to the glycoconjugate via a nitrogen linkage (see definition of N-linked glycan below).

N-linked glycans: N-linked glycans are glycans that are linked to a glycoconjugate via a nitrogen linkage. A diverse assortment of N-linked glycans exists, but is typically based on the common core pentasaccharide (Man)$_3$(GlcNAc)(GlcNAc).

O-glycan: The term "O-glycan," as used herein, refers to a polymer of sugars that has been released from a glycoconjugate but was formerly linked to the glycoconjugate via an oxygen linkage (see definition of O-linked glycan below).

O-linked glycans: O-linked glycans are glycans that are linked to a glycoconjugate via an oxygen linkage. O-linked glycans are typically attached to glycoproteins via N-acetyl-D-galactosamine (GalNAc) or via N-acetyl-D-glucosamine (GlcNAc) to the hydroxyl group of L-serine (Ser) or L-threonine (Thr). Some O-linked glycans also have modifications such as acetylation and sulfation. In some instances O-linked glycans are attached to glycoproteins via fucose or mannose to the hydroxyl group of L-serine (Ser), L-threonine (Thr), or hydroxyLysine (hLys).

Phosphorylation: As used herein, the term "phosphorylation" refers to the process of covalently adding one or more phosphate groups to a molecule (e.g., to a glycan).

Protease: The term "protease" as used herein refers to an agent that cleaves a peptide bond between sequential amino acids in a polypeptide chain. In some embodiments, a protease is an enzyme (i.e., a proteolytic enzyme). In certain embodiments, a protease is a protein (e.g., a protein enzyme) comprising one or more polypeptide chains. In certain embodiments, a protease is a chemical cleavage agent.

Protein: In general, a "protein" is a polypeptide (i.e., a string of at least two amino acids linked to one another by peptide bonds). Proteins may include moieties other than amino acids (e.g., may be glycoproteins) and/or may be otherwise processed or modified. Those of ordinary skill in the art will appreciate that a "protein" can be a complete polypeptide chain as produced by a cell (with or without a signal sequence), or can be a functional portion thereof. Those of ordinary skill will further appreciate that a protein can sometimes include more than one polypeptide chain, for example linked by one or more disulfide bonds or associated by other means.

Sialic acid: The term "sialic acid," as used herein, is a generic term for the N- or O-substituted derivatives of neuraminic acid, a nine-carbon monosaccharide. The amino group of neuraminic acid typically bears either an acetyl or a glycolyl group in a sialic acid. The hydroxyl substituents present on the sialic acid may be modified by acetylation, methylation, sulfation, and phosphorylation. The predominant sialic acid is N-acetylneuraminic acid (Neu5Ac). Sialic acids impart a negative charge to glycans, because the carboxyl group tends to dissociate a proton at physiological pH. Exemplary deprotonated sialic acids are as follows:

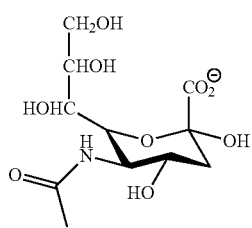

N-acetylneuraminic acid (Neu5Ac)

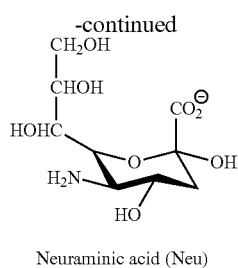

Neuraminic acid (Neu)

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena. To give but one particular example, when it is said that a treatment does not "substantially" rupture the cell membranes, it is meant to indicate that all or most of the cell membranes remain intact during and after the treatment, for example so that intracellular glycoproteins or glycopeptides are thus not released from the cells. In certain embodiments, the term "substantially," as applied to unruptured cell membranes, refers to condition wherein 15%, 10%, 9%, 8%, 7%, 6%, 5%, 4%, 3%, 2%, 1%, or fewer of the cells subjected to a particular treatment exhibit measurable ruptured cell membranes. In certain embodiments, the term "substantially," as applied to unruptured cell membranes, refers to condition wherein none of the cells subjected to a particular treatment exhibit measurable ruptured cell membranes.

DETAILED DESCRIPTION OF CERTAIN EMBODIMENTS

The present disclosure provides methods of analyzing the composition of glycans, including O-linked glycans. According to the present disclosure, methods described herein can be used to analyze a mixture of glycans, and to measure the relative levels within this mixture of specific structural groups and modifications. In many embodiments, the present disclosure provides methods involving obtaining a glycoconjugate (e.g., glycoprotein) preparation; releasing O-linked glycans from glycoconjugates in the preparation; and analyzing the released O-glycans. In some embodiments, the present disclosure provides methods involving obtaining a glycoconjugate (e.g., glycoprotein) preparation; subjecting the preparation to a treatment that removes N-linked glycans; releasing O-linked glycans from the treated preparation; and analyzing the released O-glycans.

O-Linked Glycans

In general, a glycan refers to a carbohydrate moiety which, in some embodiments, is covalently attached to a backbone molecule such as a polypeptide or lipid. Carbohydrate moieties (e.g., oligosaccharide chains) are linked to polypeptides in the endoplasmic reticulum and in the Golgi apparatus via either N-linkages or O-linkages.

O-linked oligosaccharide chains are added to polypeptides in the Golgi apparatus. The initial event in O-glycosylation is the addition of the monosaccharide GalNAc to serine, threonine, or hydroxylysine residues of the target polypeptide which is catalyzed by a GalNAc transferase (GalNAcT) (see, e.g., Wopereis et al., Clin. Chem. 52(4):574-6000, 2006; and Marth, Essentials of Glycobiology, Ch. 8 (Varki et al. eds., Cold Spring Harbor Lab. Press, 1999)). O-linked glycans can have long chains with variable termini, like N-linked glycans. However, O-linked glycans are typically less branched and often have biantennary structures. Although there is no known amino acid consensus motif for sites of O-glycosylation, such sites are often enriched for proline residues (e.g., at positions −1 and +3, relative to a glycosylated residue). Alanine, serine, and threonine residues are often adjacent to glycosylated residues.

At least seven different types of O-linked glycans are found in humans. These are listed in Table 1, and are classified based on the identity of the first sugar attached to a serine, threonine, or hydroxylysine of a polypeptide (Wopereis et al., Clin. Chem. 52(4):574-600, 2000).

TABLE 1

Types of O-linked glycans

| Type of O-linked glycan | Structure and peptide linkage |
|---|---|
| Mucin-type | (R)-GalNAcα1-Ser/Thr |
| GAG | (R)-GlcAβ1-3Galβ1-3Galβ1-4Xylβ1-Ser |
| O-linked GlcNAc | GlcNAcβ1-Ser/Thr |
| O-linked Gal | Glcα1-2 ± Galβ1-O-Lys |
| O-linked Man | NeuAcα2-3Galβ1-4GlcNAcβ1-2Manα1-Ser/Thr |
| O-linked Glc | Xylα1-3Xylα1-3 ± Glcβ1-Ser |
| O-linked Fuc | NcuAcα2-6Galβ1-4GlcNAcβ1-3 ± Fucα1-Ser/Thr Glcβ1-3Fucα1-Ser/Thr |

Mucin-type O-linked glycans include eight core structures based on differential monosaccharide linkage reactions to the initial unsubstituted GalNAcα-Ser/Thr (Table 2). The most common subtype structure, the Core 1 subtype, is formed by the addition of galactose in a β1-3 linkage to the GalNAc, which is catalyzed by a Core 1 β1-3 galactosyltransferase (Core 1 GalT). Core 1 GalTs exhibit tissue, cell, and substrate specific activities and expression patterns.

Core 2-type O-linked glycans include GlcNAc added to GalNAc in a β1-6 linkage. Core 2 O-linked glycans also require a Core 1 structure as a substrate, so a Core 2 structure also contains the Core 1 structure. Thus, a Core 1 O-linked glycan is an O-linked glycan in which Core 2 GlcNAcT has not acted. In some embodiments, Core 2 GlcNAcT enzymes can also exhibit Core 4 GlcNAcT activity and thus may use either the unmodified Core 1 or Core 3 O-linked glycan as a substrate. In some embodiments, a Core 2 O-linked glycan is a mono- or biantennary form with multiple lactosamine (Galβ1-4GlcNAc) units.

Core 3 O-linked glycan production is catalyzed by the action of Core 3 GlcNAcT activity on the initial, unsubstituted GalNAcα-Ser/Thr. In some embodiments, a Core 3 O-linked glycan is a basis for the formation of biantennary O-linked glycans by virtue of Core 4 GlcNAcT activity. Core 5 O-linked glycans (GalNAcα1-3GalNAcα-Ser/Thr) are less common than Core 1, 2, 3, and 4 O-linked glycans. Core 6 O-linked glycans (GlcNAcβ1-6GalNAcα-Ser/Thr) are also less common. Core 7 O-linked glycans (GalNAcα1-6GalNAcα-Ser/Thr) have also been described. Fucose (α1-2) linked to the GalNAcα-Ser/Thr has been observed.

In some embodiments, a core structure of a mucin-type O-linked glycan is modified by the addition of an N-acetyllactosamine unit (Galβ1-4GlcNAc; where GlcNAc is N-acetylglucosamine). In some embodiments, the N-acetyllactosamine unit is branched (e.g., by a repeating N-acetyllactosamine unit, or by a GlcNAcβ1-6 residue). In some embodiments, an N-acetyllactosamine unit is linked to a blood group determinant (e.g., an A, B, or H blood group determinant). In some embodiments, an N-acetyllactosamine unit is attached to a type 2 Lewis determinant (e.g., an Le$^x$, sialyl Lewis$^x$ (sLe$^x$), or Le$^y$ determinant).

In some embodiments, an O-linked glycan includes one or more terminal residues selected from NeuAc, Fuc, GlcNAc, and GalNAc residues.

TABLE 2

Core structures of Mucin-type O-linked glycans

| Core | Structure |
|---|---|
| 1 | Galβ1-3GalNAc |
| 2 | Galβ1-3 (GlcNAcβ1-6)GalNAc |
| 3 | GlcNAcβ1-3GalNAc |
| 4 | GlcNAcβ1-3 (GlcNAcβ1-6)GalNAc |
| 5 | GalNAcα1-3GalNAc |
| 6 | GlcNAcβ1-6GalNAc |
| 7 | GlcNAcα1-6GalNAc |
| 8 | Galα1-3GalNAc |

Glycosaminoglycan (GAG) type O-linked glycans typically attach to a serine residue of a polypeptide via the tetrasaccharide, GlcAβ1-3Galβ1-3Galβ1-4Xyl. In some embodiments a GAG type O-linked glycan is unbranched. In some embodiments, a GAG type O-linked glycan includes a disaccharide repeat (e.g., a GalNAc-glucuronic acid (GlcA) repeat, a GalNAc-Gal repeat, a GlcNAc-GlcA repeat, and/or a GlcNAc-Gal repeat). In some embodiments, GlcNAc residues of an O-linked glycan are deacetylated. In some embodiments, GlcNAc residues of an O-linked glycan are N-sulfated.

O-linked glycans are involved in diverse cellular processes such as protein stability, protein expression, protein processing, signaling, modulation of enzyme activity, cell adhesion, inflammation, cell proliferation, apoptosis, oocyte fertilization, endocytosis, and cell trafficking.

In some embodiments, an O-linked glycan influences secondary structure of a glycoprotein (e.g., the O-linked glycan disrupts an alpha-helical structure of a glycoprotein). In some embodiments, an O-linked glycan promotes agreggation of a glycoprotein (e.g., agreggation of the glycoprotein with itself, and/or with another glycoprotein). In some embodiments, an O-linked glycan maintains or promotes one or more of stability, heat resistance, hydrophilicity, or protease resistance of a glycoprotein.

In some embodiments, an O-linked glycan binds to a lectin. In some embodiments, an O-linked glycan is a selectin ligand. In some embodiments, an O-linked glycan serves as a co-receptor. In some embodiments, an O-glycosylated glycoprotein has a large number of clustered O-linked glycans.

The present disclosure encompasses the recognition that it is important to determine the characteristics, quantity, and glycosylation pattern of O-linked glycans (e.g., O-linked glycans which are conjugated to backbone molecules as glycoconjugates such as glycoproteins). Methods described herein may be used to analyze the characteristics (e.g., composition and/or structure) of any O-linked glycan.

N-Linked Glycans

Typically, N-linked oligosaccharide chains are added to glycoproteins in the lumen of the endoplasmic reticulum (see Alberts et al., *Molecular Biology of the Cell,* 1994, incorporated herein by reference). Carbohydrate moieties are added to the amino group on the side chain of an asparagine residue contained within the target consensus sequence of Asn-X-Ser/Thr, where X may be any amino acid except proline. The initial oligosaccharide chain is usually trimmed by specific glycosidase enzymes in the endoplasmic reticulum, resulting in a short, branched core oligosaccharide composed of two N-acetylglucosamine and three mannose residues.

N-linked glycans can be subdivided into three distinct groups called "high mannose type," "hybrid type," and "complex type," with a common pentasaccharide core (Manp($\alpha$-1, 6)-(Manp($\alpha$-1,3))-Manp($\beta$1,4)-GlcpNAc($\beta$1,4)-GlcpNAc ($\beta$1,N)-Asn) occurring in all three groups. Modifications to the core include, for example, additional glycosylation, providing a bisecting GlcNAc, attachment of a fucosyl residue on the innermost GlcNAc, and capping with sialic acid (Neu) residues. Structural variation of N-linked glycans mostly occurs with respect to the (up to) 4 antennae at one side of the N-linked glycans. N-linked glycans are commonly found as components of peptides and proteins (i.e., a glycoprotein).

After initial processing in the endoplasmic reticulum, glycoproteins are then transported to the Golgi where further processing may take place. Trimmed N-linked oligosaccharide chains may be modified by addition of several mannose residues, resulting in a "high-mannose oligosaccharide." Alternatively or additionally, one or more monosaccharide units of N-acetylglucosamine may be added to the core mannose subunits to form "complex oligosaccharides." Galactose may be added to N-acetylglucosamine subunits, and sialic acid subunits may be added to galactose subunits, resulting in chains that terminate with any of a sialic acid, a galactose, or an N-acetylglucosamine residue. A fucose residue may be added to an N-acetylglucosamine residue of the core oligosaccharide. Each of these additions is catalyzed by specific glycosyl transferases.

N-linked glycans are involved in a variety of cellular processes. For example, N-linked glycans contribute to proper protein folding in eukaryotic cells. Chaperone proteins in the endoplasmic reticulum (e.g., calnexin and calreticulin) bind to the three glucose residues present on the N-glycan core. Chaperone proteins typically aid in the folding of the protein to which the glycan is attached. Following proper folding, the three glucose residues are removed, and the glycan can move on to further processing reactions. If the protein fails to fold properly, the three glucose residues are reattached, allowing the protein to re-associate with chaperones. This cycle may repeat several times until a protein reaches it proper conformation. If a protein repeatedly fails to properly fold, it is usually excreted from the endoplasmic reticulum and degraded by cytoplasmic proteases.

Alternatively or additionally, N-linked glycans contribute to protein folding by steric effects. For example, cysteine residues in a peptide may be temporarily blocked from forming disulfide bonds with other cysteine residues, due to the size of a nearby glycan. Presence of an N-linked glycan, therefore, can allow a cell to control which cysteine residues will form disulfide bonds.

N-linked glycans can be involved in cell-cell interactions. For example, tumor cells frequently produce abnormal N-glycan structures, which can be recognized by the CD337 receptor on natural killer cells as a sign that the cell in question is cancerous.

N-linked glycans can be involved in targeting of degradative lysosomal enzymes to the lysosome. In particular, modification of an N-linked glycan with a mannose-6-phosphate residue can serve as a signal that the protein to which this glycan is attached should be targeted to the lysosome.

Thus, the present disclosure encompasses the recognition that it is important to determine the glycosylation pattern of N-linked glycans (e.g., N-linked glycans which are conjugated to glycoproteins). Methods described herein may be used to analyze the characteristics (e.g., composition and/or structure) of any N-linked glycan.

Glycan Preparations

The present disclosure provides methods of analyzing the structure and/or composition of individual glycans within a glycan preparation. A glycan preparation may be obtained by any method available in the art. In some embodiments, an O-linked glycan preparation is obtained from a glycoconjugate (e.g., glycoprotein) preparation. In some embodiments, an O-linked glycan preparation is obtain from a glycoprotein preparation that has been treated to remove N-linked glycans. In some embodiments, obtaining a glycan preparation optionally comprises a step of labeling the glycan preparation with a detectable label.

Glycoprotein Preparations

A glycoprotein preparation may be obtained from any source including, but not limited to, therapeutic formulations (e.g., erythropoietin, insulin, human growth hormone, etc.), commercial biological products (e.g., those presented in Table 5), and biological samples. As used herein, the term "biological sample" refers to any solid or fluid sample obtained from, excreted by or secreted by any living cell or organism, including, but not limited to, tissue culture, human or animal tissue, plants, fruits, vegetables, single-celled microorganisms (such as bacteria and yeasts) and multicellular organisms. For example, a biological sample can be a biological fluid obtained from, for example, blood, plasma, serum, urine, bile, seminal fluid, cerebrospinal fluid, aqueous or vitreous humor, or any bodily secretion, a transudate, an exudate (e.g., fluid obtained from an abscess or any other site of infection or inflammation), or fluid obtained from a joint (e.g., a normal joint or a joint affected by disease such as a rheumatoid arthritis, osteoarthritis, gout or septic arthritis). A biological sample can also be, for example, a sample obtained from any organ or tissue (including a biopsy or autopsy specimen), can comprise cells (whether primary cells or cultured cells), medium conditioned by any cell, tissue or organ, tissue culture.

A glycoprotein preparation may be received by any machine, person, or entity. In some embodiments, a glycoprotein preparation may be received by a machine, which may then perform one or more tests, processes, or refinements of the glycoprotein preparation. In some embodiments, a glycoprotein preparation may be received by a person. In some embodiments, a glycoprotein preparation may be received from an outside entity. In some embodiments, a glycoprotein preparation may be received by a person or business performing characterization services for a second person or business. For example, a business may be operated in which the business receives glycoprotein preparations to be characterized from other businesses or laboratories. A glycoprotein preparation may be preprocessed in any manner. For example, a glycoprotein preparation may be preprocessed to isolate one or more glycoforms.

O-Linked Glycan Preparation

In some embodiments, an O-linked glycan preparation is obtained by providing a glycoconjugate (e.g., glycoprotein) population and removing O-linked glycans from glycoconjugates in the population.

In some embodiments, O-linked glycans are removed from glycoconjugates (e.g., glycoproteins) by $\beta$-elimination. In some embodiments, O-linked glycans are removed from glycoconjugates (e.g., glycoproteins) by reductive $\beta$-elimination (e.g., by treatment with NaOH and NaBH$_4$, or with NH$_3$—H$_2$O and NH$_3$BH$_3$). In some embodiments, O-linked glycans are removed from glycoconjugates (e.g., glycoproteins) by non-reductive β-elimination (e.g., by treatment with LiOH, or ethylamine in aqueous solution, or $NH_3$—$H_2O$).

In some embodiments, O-linked glycans are removed from a glycoconjugate (e.g., a glycoprotein) preparation by incubating the preparation in a solution that includes alkaline tetrahydroborate. In some embodiments, tetradeuterioborate is used, e.g., to incorporate a deuterium label to facilitate detection of O-linked glycans. In various exemplary methods, a glycoconjugate preparation is incubated in a solution containing 0.8-1.0 M $NaBH_4$ and 0.05-0.1 M NaOH at 42-45° C. for 2-24 hours. A reaction to remove O-glycans can be terminated by the addition of acid (e.g., 1.0 M HCl).

In some embodiments, O-linked glycans are removed from a glycoconjugate preparation by incubating the preparation in a solution that includes NaOH. In various exemplary methods, a glycoconjugate is incubated in a solution containing 50-200 mM NaOH at 27-45° C. for 2-48 hours. A reaction to remove O-linked glycans can be terminated by the addition of acid.

In some embodiments, O-linked glycans are removed from a glycoconjugate preparation by incubating the preparation in a solution that includes $NH_4OH$. In various exemplary methods, a glycoconjugate is incubated in a solution containing 25-28% $NH_4OH$ at 45-60° C. for 2-40 hours. The reaction can be terminated by removing the $NH_4OH$ under vacuum. In some embodiments, the solution includes ammonium carbonate (e.g., at a saturating concentration). In some embodiments, the $NH_4OH$-treated preparation is treated with acid (e.g., boric acid).

In some embodiments, O-linked glycans are removed from a glycoconjugate preparation by incubating the preparation in an aqueous solution that includes ethylamine (e.g., ethylamine at about 70%) or methylamine (e.g., methylamine at about 40%), for about 4-24 hours.

In some embodiments, O-linked glycans are removed from a glycoconjugate preparation by incubating the preparation in a solution that includes $BH_3NH_3$ and $NH_3H_2O$. In various exemplary methods, a glycoconjugate preparation is incubated in a mixed solution of $BH_3NH_3/NH_3H_2O$ (e.g., 12.7 mg $BH_3NH_3$ dissolved in 2.54 ml of $NH_3.H_2O$ to make 5 mg/ml concentration). The solution is incubated at 45° C. (e.g., in a water bath) for 18 hr. The resulting solution is placed in a speed vacuum for multiple cycles with addition of methanol, dried, and redissolved in water. The solution is neutralized to pH 6~7 with 6N HCl solution. In some embodiments, the solution is applied to pretreated PGC cartridges, and eluted with 40% acetonitrile containing 0.05% TFA. Eluted O-glycans can be dried in a speed vacuum and subjected to LC-MS/MS analysis.

In some embodiments, O-linked glycans are removed from a glycoconjugate preparation by incubating the preparation in a solution that includes LiOH. In various exemplary methods, a glycoconjugate preparation is incubated in a solution that includes 0.5 M LiOH for 24-48 hours at 4° C. The solution is neutralized with acid (e.g., in 1M acetic acid) to pH 6~7.

In one exemplary method, an N-deglycosylated glycoprotein preparation is obtained by PNGase F treatment of a glycoprotein preparation, followed by C18 cartridge purification. The N-deglycosylated glycoprotein preparation is placed in a solution of 0.5 M LiOH and incubated for 48 hours at 4° C. The resulting solution is neutralized with 1M acetic acid to pH 6~7, and purified with a AG 50W-X2 cation exchange column under gravity. The sample is frozen to dryness.

As would be appreciated by one of skill in the art, the reaction times, temperature, and reagent concentrations can be optimized, e.g., based on knowledge of an O-glycan structure of a particular glycoprotein, quantification, or the characterization to be carried out. Optimization of these parameters can facilitate recovery and reduce bias of releasing glycans from one site over another.

In some embodiments, an O-linked glycan preparation is obtained from a glycoconjugate population from which N-glycans have been removed. In some embodiments, a glycoconjugate preparation is digested with a protease, e.g., before or after a treatment to remove one or both of N-linked glycans and O-linked glycans.

N-Linked Glycan Preparation

In some embodiments, an N-glycan preparation is obtained by providing a glycoconjugate (e.g., glycoprotein) population and removing N-linked glycans from the glycoconjugates of the population. In some embodiments, N-linked glycans are removed from a glycoconjugate preparation prior to removing O-linked glycans.

In some embodiments, N-linked glycans are removed from glycoconjugates by digestion. Generally, glycanases to be used in accordance with the present disclosure cleave between GlcNAc-Asn, GlcNAc-GlcNAc, or Man-GlcNAc residues of a core structure. Exemplary enzymes which can be used to remove N-linked glycans from glycoconjugates include, but are not limited to, N-glycanase F and/or N-glycanase-A, and/or Endo H.

In some embodiments, N-glycans are removed from glycoconjugates by chemical cleavage. To give but a few examples, hydrazine, sodium borohydride, and/or trifluoromethanesulfonic acid (TFMS) can be used to remove glycans from a glycoconjugate.

Labeling Glycans

In some embodiments, glycans (e.g., O-linked glycans and/or N-linked glycans that have been removed from a glycoconjugate population) can be associated with one or more detectable labels. Detectable labels are typically associated with the reducing ends of glycans. In some embodiments, detectable labels are fluorescent moieties. Exemplary fluorophores that can be used in accordance with the present disclosure include, but are not limited to, 2-aminobenzoic acid (2AA), 2-aminobenzamide (2AB), and/or 2-aminopurine (2AP). In general, fluorophores for use in accordance with the present disclosure are characterized by having reactivity with the reducing end of an oligosaccharide and/or monosaccharide under conditions that do not damage and/or destroy the glycan. In some embodiments, fluorescent moieties are attached to reducing ends directly. For example, direct attachment can be accomplished by direct conjugation by reductive amination. In some embodiments, fluorescent moieties are attached to reducing ends indirectly. For example, indirect attachment can be accomplished by a reactive linker arm.

In some embodiments, detectable labels comprise radioactive moieties or isotopically-labelled molecules. Exemplary radioactive moieties that can be used in accordance with the present disclosure include, but are not limited to, tritium ($^3H$), deuterium ($^2H$), and/or $^{35}S$. Typically, such moieties are directly attached to or otherwise associated with the fluorophore. To give but one example of a radioactive fluorophore, 2AP can be modified such that all hydrogens are deuterated. In some embodiments, glycans are labeled prior to release from a backbone (e.g., from a polypeptide backbone). In some embodiments, glycans are labeled after release from a backbone.

Digestion of Glycans

In some embodiments, the present disclosure provides methods of determining glycosylation patterns of glycoconjugates (e.g., glycoproteins) using exoglycosidases. In some embodiments, such methods involve subjecting a glycan population to one or more exoglycosidases and analyzing the structure and/or composition of the digestion products. In some embodiments, exoglycosidases used in accordance with the present disclosure recognize and cleave only one particular type of glycosidic linkage. In some embodiments, exoglycosidases used in accordance with the present disclosure recognize and cleave more than one particular type of glycosidic linkage.

Exoglycosidases

Exoglycosidases are enzymes which cleave terminal glycosidic bonds from the non-reducing end of glycans. They are typically highly specific to particular monosaccharide linkages and anomericity (α/β). In some embodiments, neighboring branching patterns can affect exoglycosidase specificity. Exoglycosidase treatment usually results in glycans of standard antennary linkages being cleaved down to the pentasaccharide core (M3N2) containing 3 mannose and 2 glcNAc residues. However, unusually-modified species (e.g., antennary or core fucosylated species, high-mannose and hybrid glycans, lactosamine-extended glycans, sulfated glycans, phosphorylated glycans, etc.) are resistant to exoglycosidase treatment and can be chromatographically resolved and quantified relative to the M3N2 pentasaccharide.

Exemplary exoglycosidases that can be used in accordance with the present disclosure include, but are not limited to, sialidase, galactosidase, hexosaminidase, fucosidase, and mannosidase. Exoglycosidases can be obtained from any source, including commercial sources (e.g., from QA-Bio, ProZyme, Roche, Sigma, NEB, EMD, Glyko, etc.). Alternatively or additionally, exoglycosidases can be isolated and/or purified from a cellular source (e.g., bacteria, yeast, plant, etc.).

In some embodiments, exoglycosidases (e.g., sialidases, galactosidases, hexosaminidases, fucosidases, and mannosidases) can be divided into multiple categories or "subsets." In some embodiments, the different subsets display different abilities to cleave different types of linkages. Table 3 presents some exemplary exoglycosidases, their linkage specificities, and the organism from which each is derived. One of ordinary skill in the art will appreciate that this is an exemplary, not a comprehensive, list of exoglycosidases, and that any exoglycosidase having any linkage specificity may be used in accordance with the present disclosure.

TABLE 3

Exoglycosidases

| Enzyme class | EC #* | Activity | Organism |
| --- | --- | --- | --- |
| α-Sialidase | 3.2.1.18 | α-2/3,6,8 (usually not linkage-specific) | Arthrobacter ureafaciens<br>Vibrio cholerae<br>Clostridium perfringens |
| | | α-2,3 (NeuAc from oligosaccharides) | Salmonella typhimurium<br>Streptococcus pneumonia |
| | | α-2/3,6 (NeuAc from complex) | Clostridium perfringens |
| β-Galactosidase | 3.2.1.23 | β-1/3,4,6 Gal linkages | Bovine testis<br>Xanthamonas species<br>Streptococcus species<br>E. coli |
| | | β-1/4,6 Gal linkages | Jack bean |
| | | β-1,4 Gal linkage | Streptococcus pneumonia |
| | | β-1,3-Gal linkage | E. coli<br>Xanthomonas species |
| | | β1/3,6-Gal linkages | Xanthomonas species<br>E. coli |
| β-Hexosaminidase | 3.2.1.52<br>3.2.1.30 | β-1/2,3,4,6 hexosamines | Streptococcus plicatus<br>Streptococcus pneumonia<br>Bacteroides<br>Jack bean |
| α-Fucosidase | 3.2.1.51<br>3.2.1.111 | α-1-3,4-Fuc (usually de-glycosylate Lewis structure) | Xanthomonas<br>Almond meal |
| | | α-1/2,3,4,6-Fuc (usually has broad specificity) | Bovine kidney<br>C. meningosepticum |
| | | α-1,6-Fuc | E. coli |
| | | α-1,2-Fuc | Xanthomonas |
| α-Mannosidase | 3.2.1.24 | α-1/2,3,6-Man | Jack bean |
| | | α-1/2,3-Man | Xanthomonas manihotis |
| | | α-1,6-Man (typically a core mannosidase) | Xanthomonas species |
| | | α-1,2-Man | Aspergillus saitoi |
| β-Mannosidase | 3.2.1.25 | α-1,4-Man | Helix pomatia |

*"EC #" refers to Enzyme Commission registration number

According to the present disclosure, a glycan population can be digested with any exoglycosidase or any set of exoglycosidases. In general, exoglycosidase reactions take place under conditions that are compatible with enzyme activity. For example, pH, temperature, reaction solution components and concentration (e.g., salt, detergent, etc.), and length of reaction time can be optimized in order to achieve a desired level of exoglycosidase activity.

In some embodiments, simultaneous digestion with multiple exoglycosidases can be used to analyze glycan structure and/or function. In some cases, simultaneous digestion can be performed in order to determine the presence of particular types of linkages and/or glycan modifications.

As another non-limiting example, glycans may be digested by subjecting a population of glycans to a first exoglycosidase for a first period of time, after which the population of glycans is subjected to a second exoglycosidase for a second period of time. Prior to treatment with the second exoglycosidase, the first exoglycosidase may optionally be removed and/or inactivated. By way of example, the first exoglycosidase may be inactivated incubating the exoglycosidase at a temperature for a time sufficient to inactivate it. Additionally or alternatively, the first exoglycosidase may be inactivated by incubating it with an inhibitor that is specific to the exoglycosidase (e.g., an antibody or other molecule that specifically binds the first exoglycosidase and inhibits its catalytic activity). Other methods of inactivating the first exoglycosidase will be known to those of ordinary skill in the art. In the case where the first exoglycosidase is inactivated by incubating it with a specific inhibitor, it will be appreciated that the presence of the inhibitor should not substantially inhibit the activity of the second exoglycosidase. In some embodiments, methods for inactivating or removing a first exoglycosidase before addition of a second exoglycosidase include heating the reaction mixture, cooling the reaction mixture, adding organic solvents, adding proteases, and/or combinations thereof. In some embodiments, the first exoglycosidase is removed from the reaction before addition of a second exoglycosidase, e.g., by chromatography, solid phase extraction cartridges, molecular weight filters, centrifugation, precipitation, and/or combinations thereof. One of ordinary skill in the art will recognize that these same principles apply for third, fourth, fifth, sixth, etc. exoglycosidases.

In some embodiments, sequential digestion with multiple exoglycosidases reveals information about glycan structure and/or composition that is different from information revealed by simultaneous digestion with the same set of exoglycosidases.

In some embodiments, sequential digestion with multiple exoglycosidases reveals information about glycan structure and/or composition that is the same information revealed by simultaneous digestion with the same set of exoglycosidases.

In some embodiments, varying the sequence in which multiple exoglycosidases are administered reveals information about glycan structure and/or composition. To give but one example, subjecting a particular glycan to (1) a sialidase, (2) a galactosidase, (3) a hexosaminidase, (4) a fucosidase, and (5) a mannosidase, in that particular order, might yield a set of digestion products that is different from the digestion products obtained by subjecting the same N-glycan to (1) a hexosaminidase, (2) mannosidase, (3) sialidase, (4) fucosidase, and (5) a sialidase, in that order. Performing both series of sequential digests, analyzing the different sets of digestion products obtained by both sequential digests, and comparing the different sets of digestion products (e.g., relative to one another and/or relative to a reference sample) may provide information about the structure and/or composition of the glycan that would not have been obtained by performing only one of the series of sequential digests and analyzing the digestion products obtained from only one of the series of sequential digests.

In some embodiments, the individual enzymes that constitute a set of enzymes to be used in sequential and/or simultaneous digests are chosen in order to maximize the information that may be obtained by performing digests. The treatments shown in Table 4 exemplify selection of enzymatic treatments to identify specific glycan modification on sialyated glycans.

TABLE 4

Exemplary Enzymatic Treatments for Identifying Modifications on Sialyated Glycans

| Examples of glycan modification to be identified | Examples of enzymatic treatments applicable for the identification of the selected glycan modification* |
|---|---|
| Polylactosamine | Comparison between sequential and simultaneous reactions with sialidase, galactosidase, galactosidase, hexosaminidase without sialidase, and N-acetylhexosaminidase. |
| Antennary fucosylation | Comparison between sequential and simultaneous treatments with sialidase, galactosidase, hexosaminidase, and fucosidase. Comparison between treatments (e.g., sequential and/or simultaneous) with α-1,3 fucosidase and α-1,6,3 fucosidase. Comparison between treatments (e.g., sequential and/or simultaneous) with fucosidase followed by galactosidase or galactosidase, followed by fucosidase Comparison between treatments (e.g., sequential and/or simultaneous) with and without fucosidase. |
| Hybrid glycan | Comparison between sequential and simultaneous reactions with sialidase, galactosidase and N-acetylhexosaminidase, hexosaminidase, and mannosidase. |
| Sulfated glycans | Comparison between sequential and simultaneous reactions with sialidase, galactosidase, galactosidase, hexosaminidase without sialidase, and N-acetylhexosaminidase. |
| Phosphorylated glycans | Comparison between treatments (e.g., sequential and/or simultaneous) with and without mannosidase. |
| Sialic acid linked to GlcNAc | Comparison between sequential and simultaneous reactions with sialidase, galactosidase, galactosidase, hexosaminidase without sialidase, and N-acetylhexosaminidase. |

In some embodiments, enzymatic treatments for identifying modifications on non-sialyated glycans can be performed as described in Table 4, except that sialidase is omitted from the reactions exemplified in Table 4.

Analysis of Glycan Structure

In various embodiments, methods in accordance with the present disclosure comprise subjecting a glycoconjugate preparation to a condition that releases a glycan, and analyzing the released glycan. In some embodiments, the methods involve releasing O-linked glycans from a glycoconjugate (e.g., glycoprotein) preparation by β-elimination (e.g., reductive β-elimination, or non-reductive β-elimination). In some embodiments the glycoconjugate is first subjected to a treatment that releases N-linked glycans from the glycoconjugate preparation. In some embodiments, released O-glycans and released N-glycans are analyzed, e.g., to determine the structure and/or identity of the glycans. In some embodiments, a sample may be removed from the glycan preparation during the course of treatment to remove N- and/or O-linked glycans. In some embodiments, a plurality of samples, which are separated in time (e.g. at regular or irregular intervals), may be removed from the glycan preparation during the course of the treatment to remove glycans. In some embodiments, a method includes treatment with at least one exoglycosidase. In some embodiments, the analyzing comprises comparing the structure and/or function of glycans in one or more of the removed samples to structure and/or function of cleaved glycans in at least one other removed sample. In some embodiments, the step of analyzing comprises comparing the structure and/or function of cleaved glycans in one or more of the removed samples to structure and/or function of cleaved glycans in a reference sample.

Structure and composition of O-linked glycans and/or N-linked glycans can be analyzed by any available method. In some embodiments, O-linked glycan and/or N-linked glycan structure and composition can be analyzed by chromatographic methods, mass spectrometry (MS) methods, chromatographic methods followed by MS, electrophoretic methods, electrophoretic methods followed by MS, nuclear magnetic resonance (NMR) methods, and combinations thereof.

In some embodiments, glycan structure and composition can be analyzed by chromatographic methods, including but not limited to, liquid chromatography (LC), high performance liquid chromatography (HPLC), ultra performance liquid chromatography (HPLC), thin layer chromatography (TLC), amide column chromatography, and combinations thereof.

In some embodiments, glycan structure and composition can be analyzed by mass spectrometry (MS) and related methods, including but not limited to, tandem MS, LC-MS, LC-MS/MS, matrix assisted laser desorption ionization mass spectrometry (MALDI-MS), Fourier transform mass spectrometry (FTMS), ion mobility separation with mass spectrometry (IMS-MS), electron transfer dissociation (ETD-MS), and combinations thereof.

In some embodiments, glycan structure and composition can be analyzed by electrophoretic methods, including but not limited to, capillary electrophoresis (CE), CE-MS, gel electrophoresis, agarose gel electrophoresis, acrylamide gel electrophoresis, SDS-polyacrylamide gel electrophoresis (SDS-PAGE) followed by Western blotting using antibodies that recognize specific glycan structures, and combinations thereof.

In some embodiments, glycan structure and composition can be analyzed by nuclear magnetic resonance (NMR) and related methods, including but not limited to, one-dimensional NMR (1D-NMR), two-dimensional NMR (2D-NMR), correlation spectroscopy magnetic-angle spinning NMR (COSY-NMR), total correlated spectroscopy NMR (TOCSY-NMR), heteronuclear single-quantum coherence NMR (HSQC-NMR), heteronuclear multiple quantum coherence (HMQC-NMR), rotational nuclear overhauser effect spectroscopy NMR (ROESY-NMR), nuclear overhauser effect spectroscopy (NOESY-NMR), and combinations thereof.

In some embodiments, techniques described herein may be combined with one or more other technologies for the detection, analysis, and or isolation of glycans or glycoconjugates. For example, in certain embodiments, glycans are analyzed in accordance with the present disclosure using one or more available methods (to give but a few examples, see Anumula, *Anal. Biochem.* 350(1):1, 2006; Klein et al., *Anal. Biochem.*, 179:162, 1989; and/or Townsend, R. R. Carbohydrate Analysis" High Performance Liquid Chromatography and Capillary Electrophoresis., Ed. Z. El Rassi, pp 181-209, 1995, each of which is incorporated herein by reference in its entirety). For example, in some embodiments, glycans are characterized using one or more of chromatographic methods, electrophoretic methods, nuclear magnetic resonance methods, and combinations thereof. Exemplary such methods include, for example, NMR, mass spectrometry, liquid chromatography, 2-dimensional chromatography, SDS-PAGE, antibody staining, lectin staining, monosaccharide quantitation, capillary electrophoresis, fluorophore-assisted carbohydrate electrophoresis (FACE), micellar electrokinetic chromatography (MEKC), exoglycosidase or endoglycosidase treatments, and combinations thereof. Those of ordinary skill in the art will be aware of other methods that can be used to characterize glycans together with the IMAC methods described herein.

In some embodiments, methods described herein allow for detection of glycan species that are present at low levels within a population of glycans. For example, the present methods allow for detection of glycan species that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of glycans.

In some embodiments, methods described herein allow for detection of particular linkages that are present at low levels within a population of glycans. For example, the present methods allow for detection of particular linkages that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of glycans.

In some embodiments, methods described herein allow for detection of relative levels of individual glycan species within a population of glycans. For example, the area under each peak of a liquid chromatograph can be measured and expressed as a percentage of the total. Such an analysis provides a relative percent amount of each glycan species within a population of glycans.

Applications

The present disclosure provides methods for analyzing the structure and/or composition of any glycan. To give but one example, the present disclosure provides methods for selectively analyzing O-linked glycans (e.g., for analyzing O-linked glycan preparations which are substantially free of N-linked glycans). The present disclosure encompasses the recognition that analyzing the glycosylation of a glycoconjugate (e.g., glycoprotein) has many potential commercial, industrial, and/or therapeutic applications.

Methods in accordance with the disclosure can be applied to glycans obtained from a wide variety of sources including, but not limited to, therapeutic formulations (e.g., erythropoietin, insulin, human growth hormone, etc.), commercial biological products (e.g., those presented in Table 5), and biological samples. A biological sample may undergo one or more analysis and/or purification steps prior to or after being analyzed according to the present disclosure. To give but a few examples, in some embodiments, a biological sample is treated with one or more proteases and/or glycosidases (e.g., so that glycans are released); in some embodiments, glycans in a biological sample are labeled with one or more detectable markers or other agents that may facilitate analysis by, for example, mass spectrometry or NMR. Any of a variety of separation and/or isolation steps may be applied to a biological sample in accordance with the present disclosure.

Methods of the present disclosure can be utilized to analyze glycans in any of a variety of states including, for instance, free glycans, glycoconjugates (e.g., glycopeptides, glycolipids, proteoglycans, etc.), cell-associated glycans (e.g., nucleus-, cytoplasm-, cell-membrane-associated glycans, etc.); glycans associated with cellular, extracellular, intracellular, and/or subcellular components (e.g., proteins); glycans in extracellular space (e.g., cell culture medium), etc.

Methods of the present disclosure may be used in one or more stages of process development for the production of a therapeutic or other commercially relevant glycoconjugate (e.g., glycoprotein) of interest. Non-limiting examples of such process development stages that can employ methods of the present disclosure include cell selection, clonal selection, media optimization, culture conditions, process conditions, and/or purification procedure. Those of ordinary skill in the art will be aware of other process development stages.

The present disclosure can also be utilized to monitor the extent and/or type of glycosylation occurring in a particular cell culture, thereby allowing adjustment or possibly termination of the culture in order, for example, to achieve a particular desired glycosylation pattern or to avoid development of a particular undesired glycosylation pattern.

The present disclosure can also be utilized to assess glycosylation characteristics of cells or cell lines that are being considered for production of a particular desired glycoconjugate (for example, even before the cells or cell lines have been engineered to produce the glycoconjugate, or to produce the glycoconjugate at a commercially relevant level).

For example, where the target glycoconjugate is a therapeutic glycoprotein, for example having undergone regulatory review in one or more countries, it will often be desirable to monitor cultures to assess the likelihood that they will generate a product with a glycosylation pattern as close to the established glycosylation pattern of the pharmaceutical product as possible, whether or not it is being produced by exactly the same route. As used herein, "close" refers to a glycosylation pattern having at least about a 75%, 80%, 85%, 90%, 95%, 98%, or 99% correlation to the established glycosylation pattern of the pharmaceutical product. In such embodiments, samples of the production culture are typically taken at multiple time points and are compared with an established standard or with a control culture in order to assess relative glycosylation.

For example, in some embodiments, methods for monitoring production of a glycoconjugate may comprise steps of (i) during production of a glycoconjugate, removing at least first and second glycan-containing samples from the production system; (ii) subjecting each of the first and second glycan-containing samples to a procedure to analyze O-linked glycans and/or N-linked glycans; and (iii) comparing the glycan products obtained from the first glycan-containing sample with those obtained from the second glycan-containing sample so that differences are determined and therefore progress of glycoconjugate production is monitored.

In some embodiments, glycan-containing samples are removed at regular intervals. In some embodiments, glycan-containing samples are removed at about 30 second, about 1 minute, about 2 minute, about 5 minute, about 10 minute, about 30 minute, about 1 hour, about 2 hour, about 3 hour, about 4 hour, about 5 hour, about 10 hour, about 12 hour, or about 18 hour intervals, or at even longer intervals. In some embodiments, glycan-containing samples are removed at irregular intervals. In some embodiments, glycan-containing samples are removed at 5 hour intervals.

In some embodiments of the present disclosure, a desired glycosylation pattern will be more extensive. For example, in some embodiments, a desired glycosylation pattern shows high (e.g., greater than about 60%, about 65%, about 70%, about 75%, about 80%, about 85%, about 90%, about 95%, about 98%, about 99%, or more) occupancy of glycosylation sites; in some embodiments, a desired glycosylation pattern shows, a high degree of branching (e.g., greater than about 60%, about 65%, about 70%, about 75%, about 80%, about 85%, about 90%, about 95%, about 98%, about 99% or more have tri or tetra-antennary structures).

In some embodiments of the present disclosure, a desired glycosylation pattern will be less extensive. For example, in some embodiments, a desired cell surface glycosylation pattern shows low (e.g., less than about 50%, about 45%, about 40%, about 35%, about 30%, about 25%, about 20%, about 15%, about 15%, about 5%, about 1%, or less) occupancy of glycosylation sites; and/or a low degree of branching (e.g., less than about 20%, about 15%, about 10%, about 5%, about 1% or less have tri or tetra-antennary structures).

In some embodiments, a desired glycosylation pattern will be more extensive in some aspects and less extensive in others. For example, it may be desirable to employ a cell line that tends to produce glycoconjugates with long, unbranched oligosaccharide chains. Alternatively, it may be desirable employ a cell line that tends to produce glycoconjugates with short, highly branched oligosaccharide chains.

In some embodiments, a desired glycosylation pattern will be enriched for a particular type of glycan structure. For example, in some embodiments, a desired glycosylation pattern will have low levels (e.g., less than about 20%, about 15%, about 10%, about 5%, about 1%, or less) of high mannose or hybrid structures, high levels (e.g., greater than about 60%, about 65%, about 70%, about 75%, about 80%, about 85%, about 90%, about 95%, about 98%, about 99%, or more) of high mannose structures, high levels (e.g., greater than about 60%, about 65%, about 70%, about 75%, about 80%, about 85%, about 90%, about 95%, about 98%, about 99%, or more; for example at least one per glycoconjugate) phosphorylated high mannose, or low levels (e.g., less than about 20%, about 15%, about 10%, about 5%, about 1%, or less) of phosphorylated high mannose.

In some embodiments, a desired glycosylation pattern will include at least about one sialic acid. In some embodiments, a desired glycosylation pattern will include a high level (e.g., greater than about 60%, about 65%, about 70%, about 75%, about 80%, about 85%, about 90%, about 95%, about 98%, about 99%, or more) of termini that are sialylated.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a sulfated glycan In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a phosphorylated glycan.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of a sialic acid linked to an N-acetylglucosamine.

In some embodiments, a desired glycosylation pattern will include a low level (e.g., less than about 20%, about 15%, about 10%, about 5%, about 1%, or less) or high level (e.g., greater than about 60%, about 65%, about 70%, about 75%, about 80%, about 85%, about 90%, about 95%, about 98%, about 99%, or more) of an acetylated glycan.

Whether or not monitoring production of a particular target glycoconjugate for quality control purposes, the present disclosure may be utilized, for example, to monitor glycosylation at particular stages of development, or under particular growth conditions.

In some embodiments, methods described herein can be used to characterize and/or control or compare the quality of therapeutic products. To give but one example, the present methodologies can be used to assess glycosylation in cells producing a therapeutic glycoconjugate product. Particularly given that glycosylation can often affect the activity, bioavailability, or other characteristics of a therapeutic glycoconjugate product, methods for assessing cellular glycosylation during production of such a therapeutic glycoconjugate product are particularly desirable. Among other things, the present disclosure can facilitate real time analysis of glycosylation in production systems for therapeutic proteins.

Representative therapeutic glycoconjugate products whose production and/or quality can be monitored in accordance with the present disclosure include, for example, any of a variety of hematologic agents (including, for instance, erythropoietin, blood-clotting factors, etc.), interferons, colony stimulating factors, antibodies, enzymes, and hormones.

Representative commercially available glycoprotein products include, for example, those presented in Table 5:

TABLE 5

Exemplary Commercially Available Glycoprotein Products

| Protein Product | Reference Drug |
| --- | --- |
| interferon gamma-1b | Actimmune ® |
| alteplase; tissue plasminogen activator | Activase ®/Cathflo ® |
| Recombinant antihemophilic factor | Advate |
| human albumin | Albutein ® |
| Laronidase | Aldurazyme ® |
| interferon alfa-N3, human leukocyte derived | Alferon N ® |
| human antihemophilic factor | Alphanate ® |
| virus-filtered human coagulation factor IX | AlphaNine ® SD |
| Alefacept; recombinant, dimeric fusion protein LFA3-Ig | Amevive ® |
| Bivalirudin | Angiomax ® |
| darbepoetin alfa | Aranesp ™ |
| Bevacizumab | Avastin ™ |
| interferon beta-1a; recombinant | Avonex ® |
| coagulation factor IX | BeneFix ™ |
| Interferon beta-1b | Betaseron ® |
| Tositumomab | Bexxar ® |
| antihemophilic factor | Bioclate ™ |
| human growth hormone | BioTropin ™ |
| botulinum toxin type A | Botox ® |
| Alemtuzumab | Campath ® |
| acritumomab; technetium-99 labeled | CEA-Scan ® |
| alglucerase; modified form of beta-glucocerebrosidase | Ceredase ® |
| imiglucerase; recombinant form of beta-glucocerebrosidase | Cerezyme ® |
| crotalidae polyvalent immune Fab, ovine | CroFab ™ |
| digoxin immune Fab, ovine | DigiFab ™ |
| Rasburicase | Elitek ® |
| Etanercept | Enbrel ® |
| epoietin alfa | Epogen ® |
| Cetuximab | Erbitux ™ |
| algasidase beta | Fabrazyme ® |
| Urofollitropin | Fertinex ™ |
| follitropin beta | Follistim ™ |
| Teriparatide | Forteo ® |
| human somatropin | GenoTropin ® |
| Glucagon | GlucaGen ® |
| follitropin alfa | Gonal-F ® |
| antihemophilic factor | Helixate ® |
| Antihemophilic Factor; Factor XIII | Hemofil ® |
| Insulin | Humalog ® |
| antihemophilic factor/von Willebrand factor complex-human | Humate-P ® |
| Somatotropin | Humatrope ® |
| Adalimumab | HUMIRA ™ |
| human insulin | Humulin ® |
| recombinant human hyaluronidase | Hylenex ™ |
| interferon alfacon-1 | Infergen ® |
| Eptifibatide | Integrilin ™ |
| alpha-interferon | Intron A ® |
| Palifermin | Kepivance |
| Anakinra | Kineret ™ |
| antihemophilic factor | Kogenate ®FS |
| insulin glargine | Lantus ® |
| granulocyte macrophage colony-stimulating factor | Leukine ®/Leukine ® Liquid |

TABLE 5-continued

Exemplary Commercially Available Glycoprotein Products

| Protein Product | Reference Drug |
| --- | --- |
| lutropin alfa, for injection | Luveris |
| OspA lipoprotein | LYMErix ™ |
| Ranibizumab | Lucentis ® |
| gemtuzumab ozogamicin | Mylotarg ™ |
| Galsulfase | Naglazyme ™ |
| Nesiritide | Natrecor ® |
| Pegfilgrastim | Neulasta ™ |
| Oprelvekin | Neumega ® |
| Filgrastim | Neupogen ® |
| Fanolcsomab | NeutroSpec ™ (formerly LeuTech ®) |
| somatropin [rDNA] | Norditropin ®/Norditropin Nordiflex ® |
| insulin; zinc suspension; | Novolin L ® |
| insulin; isophane suspension | Novolin N ® |
| insulin, regular; | Novolin R ® |
| Insulin | Novolin ® |
| coagulation factor VIIa | NovoSeven ® |
| Somatropin | Nutropin ® |
| immunoglobulin intravenous | Octagam ® |
| PEG-L-asparaginase | Oncaspar ® |
| abatacept, fully human soluable fusion protein | Orencia ™ |
| muromomab-CD3 | Orthoclone OKT3 ® |
| human chorionic gonadotropin | Ovidrel ® |
| peginterferon alfa-2a | Pegasys ® |
| pegylated version of interferon alfa-2b | PEG-Intron ™ |
| Abarelix (injectable suspension); gonadotropin-releasing hormone antagonist | Plenaxis ™ |
| epoietin alfa | Procrit ® |
| Aldesleukin | Proleukin, IL-2 ® |
| Somatrem | Protropin ® |
| dornase alfa | Pulmozyme ® |
| Efalizumab; selective, reversible T-cell blocker | Raptiva ™ |
| combination of ribavirin and alpha interferon | Rebetron ™ |
| Interferon beta 1a | Rebif ® |
| antihemophilic factor | Recombinate ® |
| rAHF/ntihemophilic factor | ReFacto ® |
| Lepirudin | Refludan ® |
| Infliximab | Remicade ® |
| Abciximab | ReoPro ™ |
| Reteplase | Retavase ™ |
| Rituximab | Rituxan ™ |
| interferon alfa-2a | Roferon-A ® |
| Somatropin | Saizen ® |
| synthetic porcine secretin | SecreFlo ™ |
| Basiliximab | Simulect ® |
| Eculizumab | Soliris ® |
| Pegvisomant | Somavert ® |
| Palivizumab; recombinantly produced, humanized mAb | Synagis ™ |
| thyrotropin alfa | Thyrogen ® |
| Tenecteplase | TNKase ™ |
| Natalizumab | Tysabri ® |
| human immune globulin intravenous 5% and 10% solutions | Venoglobulin-S ® |
| interferon alfa-n1, lymphoblastoid | Wellferon ® |
| drotrecogin alfa | Xigris ™ |
| Omalizumab; recombinant DNA-derived humanized monoclonal antibody targeting immunoglobulin-E | Xolair ® |
| Daclizumab | Zenapax ® |
| ibritumomab tiuxetan | Zevalin ™ |
| Somatotropin | Zorbtive ™ (Serostim ®) |

In some embodiments, the disclosure provides methods in which glycans from different sources or samples are compared with one another. In some such examples, multiple samples from the same source are obtained over time, so that changes in glycosylation patterns (and particularly in cell surface glycosylation patterns) are monitored. In some embodiments, one of the samples is a historical sample or a record of a historical sample (e.g., as in batch release testing of pharmaceutical products). In some embodiments, one of the samples is a reference sample.

In some embodiments, glycans from different cell culture samples prepared under conditions that differ in one or more selected parameters (e.g., cell type, culture type [e.g., continuous feed vs batch feed, etc.], culture conditions [e.g., type of media, presence or concentration of particular component of particular medium (a), osmolarity, pH, temperature, timing or degree of shift in one or more components such as osmolarity, pH, temperature, etc.], culture time, isolation steps, etc.) but are otherwise identical, are compared, so that effects of the selected parameter on glycosylation patterns are determined. In certain embodiments, glycans from different cell culture samples prepared under conditions that differ in a single selected parameter are compared so that effects of the single selected parameter on glycosylation patterns is determined. Among other applications, therefore, use of techniques as described herein may facilitate determination of the effects of particular parameters on glycosylation patterns in cells.

In some embodiments, glycans from different batches of a glycoconjugate of interest (e.g., a therapeutic glycoprotein), whether prepared by the same method or by different methods, and whether prepared simultaneously or separately, are compared. In such embodiments, the present disclosure facilitates quality control of glycoconjugate preparation. Alternatively or additionally, some such embodiments facilitate monitoring of progress of a particular culture producing a glycoconjugate of interest (e.g., when samples are removed from the culture at different time points and are analyzed and compared to one another). In some examples, multiple samples from the same source are obtained over time, so that changes in glycosylation patterns are monitored. In some embodiments, glycan-containing samples are removed at about 30 second, about 1 minute, about 2 minute, about 5 minute, about 10 minute, about 30 minute, about 1 hour, about 2 hour, about 3 hour, about 4 hour, about 5 hour, about 10 hour, about 12 hour, or about 18 hour intervals, or at even longer intervals. In some embodiments, glycan-containing samples are removed at irregular intervals. In some embodiments, glycan-containing samples are removed at 5 hour intervals.

In some embodiments, methods in accordance with the disclosure may be used to monitor the glycosylation pattern of glycoconjugates during the course of their production by cells. For example, production of a glycoconjugate (e.g., commercial production) may involve steps of (1) culturing cells that produce the glycoconjugate, (2) obtaining samples at regular or irregular intervals during the culturing, and (3) analyzing the glycosylation pattern of produced glycoconjugate(s) in obtained sample(s). In some embodiments, such methods may comprise a step of comparing the glycosylation patterns of produced glycoconjugate(s) in obtained samples to one another. In some embodiments, such methods may comprise a step of comparing glycosylation patterns of produced glycoconjugate(s) in obtained sample(s) to the glycosylation pattern of a reference sample.

In any of these embodiments, features of glycan analysis can be recorded, for example in a quality control record. As indicated above, in some embodiments, a comparison is with a historical record of a prior, or standard batch and/or with a reference sample of glycoprotein.

In some embodiments, glycans from different batches of a glycoconjugate of interest (e.g., a therapeutic glycoprotein), whether prepared by the same method or by different methods, and whether prepared simultaneously or separately, are compared to one another and/or to a reference sample. In some embodiments, batch-to-batch comparison may comprise steps of (i) providing a first glycan preparation from a first batch of the glycoconjugate; (ii) providing a second glycan preparation from a second batch of the glycoconjugate; (iii) subjecting each of the first and second glycan preparations to a procedure to release O-linked glycans (e.g., reducing or non-reducing β-elimination); and (iv) comparing the glycans obtained from the first glycan preparation with the glycans obtained from the second preparation so that consistency of the two batches is assessed. In some embodiments, glycan preparations can be provided by removing at least one N-linked glycan from at least one glycoconjugate from a batch and, optionally, isolating removed N-linked glycans. In some embodiments, glycan preparations may be labeled as described herein (e.g., fluorescently and/or radioactively; e.g., prior to and/or after isolation).

In some embodiments, the present disclosure facilitates quality control of glycoconjugate preparation. Features of the glycan analysis can be recorded, for example in a quality control record. As indicated above, in some embodiments, a comparison is with a historical record of a prior or standard batch of glycoconjugate. In some embodiments, a comparison is with a reference glycoconjugate sample.

In certain embodiments, the present disclosure may be utilized in studies to modify the glycosylation characteristics of a cell, for example to establish a cell line and/or culture conditions with one or more desirable glycosylation characteristics. Such a cell line and/or culture conditions can then be utilized, if desired, for production of a particular target glycoconjugate (e.g., glycoprotein) for which such glycosylation characteristic(s) is/are expected to be beneficial.

In certain embodiments, techniques in accordance with the disclosure are applied to glycans that are present on the surface of cells. In some such embodiments, the analyzed glycans are substantially free of non-cell-surface glycans. In some such embodiments, the analyzed glycans, when present on the cell surface, are present in the context of one or more cell surface glycoconjugates (e.g., glycoproteins or glycolipids). In certain embodiments, the glycosylation pattern of a membrane-bound or transmembrane cell-surface glycoprotein can be determined by (1) liberating the glycoprotein by treatment with one or more proteases; (2) digesting the liberated glycoprotein with an N-glycanase; (3) treating the digested glycoprotein with an agent that releases O-linked glycans according to any of the methods described herein; and (4) analyzing the glycans using any method available to one of ordinary skill in the art.

In some particular embodiments, cell surface glycans are analyzed in order to assess glycosylation of one or more target glycoconjugates of interest, particularly where such target glycoconjugates are not cell surface glycoproteins. In some embodiments, one can monitor glycosylation of a target glycoconjugate without isolating the glycoconjugate itself. In certain embodiments, the present disclosure provides methods of using cell-surface glycans as a readout of or proxy for glycan structures on an expressed glycoconjugate of interest. In certain embodiments, such methods include, but are not limited to, post process, batch, screening or "in line" measurements of product quality. Such methods can provide for an independent measure of the glycosylation pattern of a produced glycoconjugate of interest using a byproduct of the production reaction (e.g., the cells) without requiring the use of destruction of any produced glycoconjugate. Furthermore, methods in accordance with the disclosure can avoid the effort required for isolation of product and the potential selection of product glycoforms that may occur during isolation.

In certain embodiments, techniques in accordance with the disclosure are applied to glycans that are secreted from cells. In some such embodiments, the analyzed glycans are produced by cells in the context of a glycoconjugate (e.g., a glycoprotein or glycolipid).

According to the present disclosure, techniques described herein can be used to detect desirable or undesirable glycans, for example to detect or quantify the presence of one or more contaminants in a product, or to detect or quantify the presence of one or more active or desired species.

In various embodiments the methods can be used to detect biomarkers indicative of, e.g., a disease state, prior to the appearance of symptoms and/or progression of the disease state to an untreatable or less treatable condition, by detecting one or more specific glycans whose presence or level (whether absolute or relative) may be correlated with a particular disease state (including susceptibility to a particular disease) and/or the change in the concentration of such glycans over time.

In certain embodiments, methods described herein facilitate detection of glycans that are present at very low levels in a source (e.g., a biological sample, glycan preparation, etc.). In such embodiments, it is possible to detect and/or optionally quantify the levels of glycans that are present at levels less than about 10%, 5%, 4%, 3%, 2%, 1.5%, 1%, 0.75%, 0.5%, 0.25%, 0.1%, 0.075%, 0.05%, 0.025%, or 0.01% within a population of glycans. In some embodiments, it is possible to detect and/or optionally quantify the levels of glycans comprising between 0.1% and 5%, e.g., between 0.1% and 2%, e.g., between 0.1% and 1% of a glycan preparation. In certain embodiments, it is possible to detect and/or optionally quantify the levels of cell surface glycans at between about 0.1 fmol to about 1 mmol.

In some embodiments, methods described herein allow for detection of particular linkages that are present at low levels within a population of glycans. For example, the present methods allow for detection of particular linkages that are present at levels less than 10%, less than 5%, less than 4%, less than 3%, less than 2%, less than 1.5%, less than 1%, less than 0.75%, less than 0.5%, less than 0.25%, less than 0.1%, less than 0.075%, less than 0.05%, less than 0.025%, or less than 0.01% within a population of glycans.

In some embodiments, methods described herein allow for detection of relative levels of individual glycan species within a population of glycans. For example, the area under each peak of a liquid chromatograph can be measured and expressed as a percentage of the total. Such an analysis provides a relative percent amount of each glycan species within a population of glycans.

The present disclosure will be more specifically illustrated with reference to the following examples. However, it should be understood that the present disclosure is not limited by these examples in any manner.

EXAMPLES

Example 1

Exemplary Methods for Characterization of Glycoprotein Preparations

FIG. 1 is a schematic diagram of an exemplary entire sample workflow applied to a smaller (less than 30 kDa) and larger (greater than 30 kDa) glycoprotein, in aim to obtain N-glycans, O-glycans, and naked protein. This integrated workflow is applicable to any glycoprotein to recover N-linked and O-linked glycans, and naked protein. FIG. 2 is a schematic diagram of an exemplary analytics matrix which can be utilized to evaluate this workflow and as a measure of the quality of samples derived from each step of the workflow.

The current integrated sample workflow can include the following steps. A known amount of glycoprotein is completely N-deglycosylated with PNGase F. The resulting sample mixture contains N-glycans and N-deglycosylated protein. The N-deglycosylated protein is further used to release O-glycans through $\beta$-elimination under alkaline conditions. Finally O-glycans are obtained separately from N-glycans and naked protein. All resulting samples from this integrated workflow are subjected to various downstream analyses as shown in FIG. 2.

The reproducible, reliable workflow allows thorough characterization of glycoproteins and ensures sample structure integrity. This workflow provides an avenue to selectively characterize both N-glycan and O-glycan structure of a sample glycoprotein.

This workflow was applied to CTLA4Ig. N-glycans and deglycosylated protein fractions of CTLA4Ig were separated by semi-preparative size exclusion chromatography-high performance liquid chromatography (SEC-HPLC), peak collection and lyophilization. PGC cartridge isolation can be used for smaller glycoproteins in place of SEC-HPLC. FIG. 3 is a representative chromatogram of a CTLA4Ig deglycosylation mixture prepared by SEC-HPLC. FIG. 4 shows SDS-PAGE analysis of fraction of CTLA4Ig deglycosylation mixtures after SEC-HPLC. As expected, fractions 3 and 4 were not visualized by SDS-PAGE because they are identified as glycans and reducing reagent, respectively.

Example 2

Exemplary Method for O-Glycan Analysis of a Glycoprotein

An exemplary method for O-glycan analysis of a glycoprotein is depicted schematically in FIG. 5. An exemplary method for generating N- and O-glycans from the same sample workflow is shown in FIG. 6. In experiments that followed the method shown in FIG. 5, Orencia glycoproteins and a second preparation of glycoproteins were deglycosylated by PNGase F. All N-glycans were removed and de-N-glycosylated glycoproteins were isolated either by $C_{18}$ cartridge or SEC-HPLC.

Using the de-N-glycosylated Orencia protein, nonreductive $\beta$-elimination was performed under alkaline solution conditions of ammonia/alkylamine at 30-40° C. for 6-18 h to release O-glycans. O-glycans were recovered immediately through PGC-cartridge and used for fluorescent labeling. 2AB-labeling of O-glycans was performed at 40° C. for 8 h. The 2AB-labeled O-glycans were separated from free 2AB by passage through Glyco Clean-S cartridge.

O-glycan release conditions (e.g., reaction time, temperature, and reagent concentration) were optimized to reduce peel-off, and to pursue a complete release. One set of optimized conditions used to minimize peel-off involved release of glycans with LiOH. Specifically, the conditions included incubation in 0.1 M LiOH for 24-48 hours at 4° C. 2AB-labeled O-glycans were analyzed by amide LC-MS. More than 20 O-glycans for the second glycoproteins were identified and quantified based on fluorescence readout (EX=380 nm, EM=420 nm).

Using a second de-N-glycosylated glycoprotein preparation, reductive $\beta$-elimination to release O-glycans was performed with ammonia/BH3 complex reducing agent at 30-40° C. for 18-24 hours. Reduced O-glycan alditols were recovered through PGC cartridge. Reduced O-glycans were analyzed by PGC-LC-MS, more than 20 O-glycans were detected and relatively based on UV_206 nm.

A third glycoprotein preparation containing Fetuin was exposed to three different treatments. One was a non reductive β-elimination treatment with LiOH at 4° C. The second treatment used Ludger's hydrazinolysis method. The third treatment employed a Ludger Orela glycan release kit. Glycans from these preparations were labeled with 2AB, followed by analysis by normal phase HPLC. The results are shown in FIG. 7. The number of peaks observed indicated completeness of release of O-glycans and lack of bias in the new reaction method.

Glycan profiling in these experiments involved identification of peaks by MS, analysis of MS peak height (e.g., for representation of glycan quantity), and analysis of the number of peaks to identify the potential number of species in a sample. MS also was used to identify peel-off structures and facilitated development and selection of conditions to minimize peel-off of O-glycan structures.

EQUIVALENTS AND SCOPE

Those skilled in the art will recognize, or be able to ascertain using no more than routine experimentation, many equivalents to specific embodiments in accordance with the disclosure, described herein. The scope of the present disclosure is not intended to be limited to the above Description, but rather is as set forth in the appended claims.

Those skilled in the art will recognize, or be able to ascertain using no more than routine experimentation, many equivalents to the specific embodiments in accordance with the disclosure described herein. The scope of the present disclosure is not intended to be limited to the above Description, but rather is as set forth in the appended claims.

In the claims articles such as "a," "an," and "the" may mean one or more than one unless indicated to the contrary or otherwise evident from the context. Thus, for example, reference to "a cell" or "the cell" includes reference to one or more cells known to those skilled in the art, and so forth. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process. Furthermore, it is to be understood that the disclosure encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the disclosure, or aspects in accordance with the disclosure, is/are referred to as comprising particular elements, features, etc., certain embodiments in accordance with the disclosure or aspects in accordance with the disclosure consist, or consist essentially of, such elements, features, etc. For purposes of simplicity those embodiments have not been specifically set forth in haec verba herein. It is noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments in accordance with the disclosure, to the tenth of the unit of the lower limit of the range, unless the context clearly dictates otherwise.

In addition, it is to be understood that any particular embodiment of the present disclosure that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions in accordance with the disclosure (e.g., any exoglycosidase, any glycosidic linkage, any reaction condition, any method of purification, any method of product analysis, etc.) can be excluded from any one or more claims, for any reason, whether or not related to the existence of prior art.

The publications discussed above and throughout the text are provided solely for their disclosure prior to the filing date of the present application. Nothing herein is to be construed as an admission that the inventors are not entitled to antedate such disclosure by virtue of prior disclosure.

What is claimed is:

1. A method comprising:
   providing a first glycoprotein preparation of a therapeutic glycoprotein comprising at least one O-linked glycan;
   subjecting the first glycoprotein preparation to a de-N-glycosylation treatment that removes N-glycans from the glycoprotein preparation;
   releasing at least one O-linked glycan from a first portion of the treated first glycoprotein preparation by reductive β-elimination,
   releasing at least one O-linked glycan from a second portion of the treated first glycoprotein preparation by non-reductive β-elimination; and
   analyzing the released O-linked glycans from the first portion of the treated first glycoprotein preparation and analyzing the released O-linked glycans from the second portion of the treated first glycoprotein preparation.

2. The method of claim 1, wherein released O-glycans from the first or second portions of the treated glycoprotein are labeled.

3. The method of claim 1, further comprising repeating the method with a second glycoprotein preparation of a therapeutic glycoprotein, wherein the second glycoprotein preparation comprises a therapeutic glycoprotein having an amino acid sequence at least 85% identical to an amino acid sequence of the therapeutic glycoprotein in the first glycoprotein preparation.

4. The method of claim 3, further comprising a step of comparing a result of the analysis of the at least one released O-linked glycan obtained from the first glycoprotein preparation with a result of the analysis of the at least one released O-linked glycan obtained from the second glycoprotein preparation.

5. The method of claim 3, wherein the first and second glycoprotein preparations are preparations of the same glycoprotein.

6. The method of claim 3, wherein the first and second glycoprotein preparations are prepared under different conditions.

7. The method of claim 3, wherein the different preparation conditions differ in one or more cell culture parameters selected from the group consisting of continuous feed, batch fee, media, medium, osmolarity, pH, temperature culture time and isolation steps.

8. The method of claim 3, wherein the first and second glycoprotein preparations are preparations from different batches of the glycoprotein prepared by the same method.

9. The method of claim 3, wherein the first and second glycoprotein preparations are preparations from different batches of the glycoprotein prepared by a different method.

10. The method of claim 3, wherein the step of comparing comprises comparing the first results with a historical record of the second results.

11. The method of claim 3 wherein the second glycoprotein preparation comprises a reference glycoprotein.

12. The method of claim 1, wherein the therapeutic glycoprotein is selected from the group consisting of hematologic agents, interferons, colony stimulating factors, antibodies, enzymes and hormones.

13. The method of claim 1, wherein the therapeutic glycoprotein is an antibody.

14. The method of claim 1, wherein the therapeutic glycoprotein is selected from the group consisting of interferon gamma-1b, alteplase; tissue plasminogen activator, Recombinant antihemophilic factor, human albumin, Laronidase, interferon alfa-N3, human leukocyte derived, human antihemophilic factor, virus-filtered human coagulation factor IX, Alefacept; recombinant, dimeric fusion protein LFA3-Ig, Bivalirudin, darbepoetin alfa, Bevacizumab, interferon beta-1a; recombinant, coagulation factor IX, Interferon beta-1b, Tositumomab, antihemophilic factor, human growth hormone, botulinum toxin type A, Alemtuzumab, acritumomab; technetium-99 labeled, alglucerase; modified form of beta-glucocerebrosidase, imiglucerase; recombinant form of beta-glucocerebrosidase, crotalidae polyvalent immune Fab, ovine, digoxin immune Fab, ovine, Rasburicase, Etanercept, epoietin alfa, Cetuximab, algasidase beta, Urofollitropin, follitropin beta, Teriparatide, human somatropin, Glucagon, follitropin alfa, antihemophilic factor, Antihemophilic Factor; Factor XIII, Insulin, antihemophilic factor/von Willebrand factor complex-human, Somatotropin, Adalimumab, human insulin, recombinant human hyaluronidase, interferon alfacon-1, Eptifibatide, alpha-interferon, Palifermin, Anakinra, antihemophilic factor, insulin glargine, granulocyte macrophage colony-stimulating factor, lutropin alfa, for injection, OspA lipoprotein, Ranibizumab, gemtuzumab ozogamicin, Galsulfase, Nesiritide, Pegfilgrastim, Oprelvekin, Filgrastim, Fanolesomab, somatropin [rDNA], insulin; zinc suspension;, insulin; isophane suspension, insulin, regular;, Insulin, coagulation factor VIIa, Somatropin, immunoglobulin intravenous, PEG-L-asparaginase, abatacept, fully human soluable fusion protein, muromomab-CD3, human chorionic gonadotropin, peginterferon alfa-2a, pegylated version of interferon alfa-2b, Abarelix (injectable suspension); gonadotropin-releasing hormone antagonist, epoietin alfa, Aldesleukin, Somatrem, dornase alfa, Efalizumab; selective, reversible T-cell blocker, combination of ribavirin and alpha interferon, Interferon beta 1a, antihemophilic factor, rAHF/ntihemophilic factor, Lepirudin, Infliximab, Abciximab, Reteplase, Rituximab, interferon alfa-2a, Somatropin, synthetic porcine secretin, Basiliximab, Eculizumab, Pegvisomant, Palivizumab; recombinantly produced, humanized mAb, thyrotropin alfa, Tenecteplase, Natalizumab, human immune globulin intravenous 5% and 10% solutions, interferon alfa-n1, lymphoblastoid, drotrecogin alfa, Omalizumab; recombinant DNA-derived humanized monoclonal antibody targeting immunoglobulin-E, Daclizumab, ibritumomab tiuxetan and Somatotropin.

* * * * *